US011887306B2

(12) United States Patent
Cooper et al.

(10) Patent No.: US 11,887,306 B2
(45) Date of Patent: Jan. 30, 2024

(54) SYSTEM AND METHOD FOR INTRAOPERATIVELY DETERMINING IMAGE ALIGNMENT

(71) Applicant: Depuy Synthes Products, Inc., Raynham, MA (US)

(72) Inventors: Andrew J. Cooper, Largo, FL (US); Noah D. Wollowick, Westport, CT (US)

(73) Assignee: DePuy Synthes Products, Inc., Raynham, MA (US)

( * ) Notice: Subject to any disclaimer, the term of this patent is extended or adjusted under 35 U.S.C. 154(b) by 312 days.

(21) Appl. No.: 17/400,104

(22) Filed: Aug. 11, 2021

(65) Prior Publication Data

US 2023/0050141 A1 Feb. 16, 2023

(51) Int. Cl.
*A61B 34/10* (2016.01)
*G06T 7/00* (2017.01)
*G06T 7/33* (2017.01)

(52) U.S. Cl.
CPC ............ *G06T 7/0014* (2013.01); *A61B 34/10* (2016.02); *G06T 7/33* (2017.01); *A61B 2034/102* (2016.02);
(Continued)

(58) Field of Classification Search
CPC ..................... G06T 7/0014; G06T 7/33; G06T 2207/10121; G06T 2207/30008;
(Continued)

(56) References Cited

U.S. PATENT DOCUMENTS 5,715,836 A 2/1998 Kliegis et al.
6,205,411 B1 3/2001 DiGioia, III et al.
(Continued)

FOREIGN PATENT DOCUMENTS

CN 104244860 A 12/2014
EP 1 188 421 A2 3/2002
(Continued)

OTHER PUBLICATIONS

Extended European Search Report for EP 15755633.3 dated Sep. 18, 2017.
(Continued)

*Primary Examiner* — Charlotte M Baker
(74) *Attorney, Agent, or Firm* — Barnes & Thornburg LLP

(57) ABSTRACT

Disclosed embodiments determine, at an early stage, suitability of an intraoperative image for further intraoperative surgical analysis. The determination of suitability may be made using a first angle (such as a first obturator angle) based on at least three pelvic feature points in a preoperative image, a corresponding second angle (such as a corresponding second obturator angle) based on at least three corresponding pelvic feature points in an intraoperative image, and by comparing the first angle and the corresponding second angle to determine intraoperative image suitability. The first intra-operative image is indicated as suitable for further intraoperative analysis when an absolute value of a difference between the first angle and the corresponding second angle does not exceed a threshold. When the intraoperative image is determined as unsuitable for further intraoperative analysis, an indication of a movement direction for a fluoroscopy camera used to capture the intraoperative image is provided.

20 Claims, 30 Drawing Sheets

(52) U.S. Cl.
CPC .............. *G06T 2207/10121* (2013.01); *G06T 2207/30008* (2013.01)

(58) Field of Classification Search
CPC ... A61B 34/10; A61B 2034/102; A61B 34/25; A61B 2034/108; A61B 2034/252; A61B 2034/254; A61B 2090/376; A61B 90/37
USPC ....................................................... 382/128
See application file for complete search history.

(56) References Cited

U.S. PATENT DOCUMENTS

| | | | |
|---|---|---|---|
| 6,614,453 B1 | 9/2003 | Suri et al. | |
| 8,249,318 B2 | 8/2012 | Schmitt et al. | |
| 8,311,791 B1 | 11/2012 | Avisar | |
| 8,484,001 B2 | 7/2013 | Glozman et al. | |
| 8,635,082 B2 | 1/2014 | Woods et al. | |
| 8,831,324 B2 | 9/2014 | Penenberg | |
| 8,861,818 B2* | 10/2014 | Ito .......................... | A61B 34/10 382/128 |
| 8,917,290 B2 | 12/2014 | Beck | |
| 10,182,871 B2 | 1/2019 | Wollowick et al. | |
| 10,610,305 B2 | 4/2020 | Wollowick et al. | |
| 10,733,914 B2 | 8/2020 | Wollowick et al. | |
| 10,758,198 B2 | 9/2020 | Wollowick et al. | |
| 10,765,384 B2 | 9/2020 | Wollowick et al. | |
| 10,959,782 B2 | 3/2021 | Wollowick et al. | |
| 11,318,025 B2 | 5/2022 | Schipper et al. | |
| 11,534,127 B2 | 12/2022 | Wollowick et al. | |
| 11,642,174 B2 | 5/2023 | Wollowick et al. | |
| 2003/0176860 A1 | 9/2003 | Kazuo et al. | |
| 2004/0087852 A1 | 5/2004 | Chen et al. | |
| 2004/0171924 A1 | 9/2004 | Mire et al. | |
| 2005/0015005 A1 | 1/2005 | Kockro | |
| 2005/0054917 A1 | 3/2005 | Kitson | |
| 2005/0203384 A1 | 9/2005 | Sati et al. | |
| 2006/0098047 A1 | 5/2006 | Silverbrook | |
| 2006/0293614 A1 | 12/2006 | Radinsky et al. | |
| 2007/0015999 A1 | 1/2007 | Heldreth et al. | |
| 2007/0066917 A1 | 3/2007 | Hodorek et al. | |
| 2007/0078678 A1 | 4/2007 | DiSilvestro et al. | |
| 2008/0021299 A1 | 1/2008 | Meulink | |
| 2008/0056552 A1 | 3/2008 | Muller | |
| 2008/0075348 A1 | 3/2008 | Rappaport et al. | |
| 2008/0101682 A1 | 5/2008 | Blanford et al. | |
| 2008/0120262 A1 | 5/2008 | Habets et al. | |
| 2008/0161680 A1 | 7/2008 | von Jako et al. | |
| 2008/0255584 A1 | 10/2008 | Beverland et al. | |
| 2009/0089034 A1 | 4/2009 | Penney et al. | |
| 2009/0216230 A1 | 8/2009 | Pizarro | |
| 2009/0234217 A1 | 9/2009 | Mire et al. | |
| 2010/0030231 A1 | 2/2010 | Revie et al. | |
| 2010/0300231 A1 | 2/2010 | Revie et al. | |
| 2010/0198351 A1 | 8/2010 | Meulink | |
| 2010/0249507 A1 | 9/2010 | Prisco et al. | |
| 2010/0250571 A1 | 9/2010 | Pierce et al. | |
| 2010/0256479 A1 | 10/2010 | Park et al. | |
| 2011/0012905 A1 | 1/2011 | Kawahara | |
| 2011/0082367 A1 | 4/2011 | Regazzoni | |
| 2011/0093087 A1 | 4/2011 | McMahon et al. | |
| 2011/0214279 A1 | 9/2011 | Park et al. | |
| 2011/0268325 A1 | 11/2011 | Teichman et al. | |
| 2011/0313424 A1 | 12/2011 | Bono et al. | |
| 2011/0319941 A1 | 12/2011 | Bar et al. | |
| 2012/0016269 A1 | 1/2012 | Moctezuma de la Barrera | |
| 2012/0141034 A1 | 6/2012 | Iannotti et al. | |
| 2012/0157887 A1 | 6/2012 | Fanson et al. | |
| 2012/0194505 A1 | 8/2012 | Beck | |
| 2012/0194666 A1 | 8/2012 | Jackson | |
| 2012/0209394 A1 | 8/2012 | Bojarski et al. | |
| 2013/0046310 A1 | 2/2013 | Ranawat et al. | |
| 2013/0053858 A1 | 2/2013 | Penenberg | |
| 2013/0060146 A1* | 3/2013 | Yang ....................... | G01B 11/25 600/476 |
| 2013/0072821 A1 | 3/2013 | Odermatt et al. | |
| 2013/0135721 A1 | 5/2013 | An et al. | |
| 2013/0190887 A1 | 7/2013 | Fanson et al. | |
| 2013/0197687 A1 | 8/2013 | Pavlovskaia et al. | |
| 2013/0296078 A1 | 11/2013 | Solheim et al. | |
| 2013/0304429 A1 | 11/2013 | Haimerl | |
| 2014/0003700 A1 | 1/2014 | Hermosillo Valadez et al. | |
| 2014/0062863 A1 | 3/2014 | Yu et al. | |
| 2014/0073907 A1 | 3/2014 | Kumar et al. | |
| 2014/0303938 A1 | 10/2014 | Schoenefeld et al. | |
| 2014/0378828 A1 | 12/2014 | Penenberg et al. | |
| 2015/0117608 A1 | 4/2015 | Lytle et al. | |
| 2015/0150523 A1 | 6/2015 | Sirpad et al. | |
| 2015/0238271 A1 | 8/2015 | Wollowick et al. | |
| 2015/0257846 A1 | 9/2015 | Kubiak et al. | |
| 2016/0100909 A1 | 4/2016 | Wollowick et al. | |
| 2016/0128654 A1 | 5/2016 | Wollowick et al. | |
| 2016/0225192 A1 | 8/2016 | Jones et al. | |
| 2016/0277650 A1 | 9/2016 | Nagaraja et al. | |
| 2017/0054663 A1 | 2/2017 | Geiger et al. | |
| 2020/0085510 A1 | 3/2020 | Wollowick et al. | |
| 2020/0100751 A1 | 4/2020 | Wollowick et al. | |
| 2020/0352529 A1 | 11/2020 | Wollowick et al. | |
| 2021/0196390 A1 | 7/2021 | Wollowick et al. | |
| 2021/0361252 A1 | 11/2021 | Wollowick et al. | |
| 2022/0211446 A1 | 7/2022 | Wollowick et al. | |
| 2022/0323159 A1* | 10/2022 | Boettner ................... | A61F 2/32 |
| 2023/0277331 A1 | 9/2023 | Beck et al. | |

FOREIGN PATENT DOCUMENTS

| | | |
|---|---|---|
| EP | 1 406 203 A2 | 4/2004 |
| EP | 3511905 B1 | 11/2021 |
| JP | 2004105551 A | 4/2004 |
| JP | 2005-130928 | 5/2005 |
| JP | 2005185767 A | 7/2005 |
| JP | 2007151742 A | 6/2007 |
| JP | 2008515512 A | 5/2008 |
| JP | 2009503634 A | 1/2009 |
| JP | 2009136384 A | 6/2009 |
| JP | 2010088892 A | 4/2010 |
| JP | 2011512908 A | 4/2011 |
| JP | 2012-020133 | 2/2012 |
| WO | WO-2007-009263 A1 | 1/2007 |
| WO | WO 2011/134083 A1 | 3/2011 |
| WO | 2013049534 A1 | 4/2013 |
| WO | WO-2013-175471 A1 | 11/2013 |
| WO | WO 2014-008613 A1 | 1/2014 |
| WO | WO 2014/025305 A1 | 2/2014 |
| WO | WO2014-127354 | 8/2014 |
| WO | WO-2015-130848 A1 | 9/2015 |

OTHER PUBLICATIONS

International Search Report and Written Opinion for PCT/US2015/017603—dated Jun. 10, 2015.
Japanese office action and translation for Japanese Application No. 2016-570943, Examiner's Notice dated Dec. 27, 2018, dated Jan. 1, 2019, pp. 1-13.
International Preliminary Report on Patentability for PCT/US2016/067587 dated Jun. 19, 2018.
International Search Report or PCT/US2016/067587 dated May 25, 2017.
Supplementary European Search Report for EP 17739110 dated Jun. 25, 2019.
Supplementary European Search Report for EP 16876926.3 (corresponding to PCT/US2016/067587) dated Oct. 23, 2019.
Baumgaertner et al., "The Value of the Tip-Apex Distance in Predicting Failure of Fixation of Peritrochanteric Fractures of the Hip," J. of Bone & Joint Surgery, 1995.
De Bruijn et al., Reliability of Predictors for Screw Cutout in Intertrochanteric Hip Fractures, Journal of Bone and Joint Surgery, 2012, Bol. 94, pp. 1266-1272.
Matta et al., Single-incision Anterior Approach for Total Hip Arthroplasty on an Orthopaedic Table, Clin. Ortho. and Related Research, 2005, pp. 115-124, vol. 441, Lippincott W.

(56) References Cited

OTHER PUBLICATIONS

Liaw et al., A New Tool for Measuring Cup Orientation in Total Hip Arthroplasties from Plain Radiographs, Clin. Ortho. and Related Research, 2006, pp. 134-139, vol. 451, Lippincott Wiliams & Wilkins.

Mann et al., Radiographic Evaluation of the Wrist: What Does the Hand Surgeon Want to Know?, Radiology, 1992, pp. 15-24, vol. 184.

Branislav, Jaramaz et al., CupAlign: Computer-Assisted Postoperative Radiographic Measurement of Acetabular Components Following Total Hip Arthroplasty, Jan. 1, 2006, pp. 876 pp. 876-882, Medical Image Computing and Computer Assisted Intervention 1999, 2nd Int'l Conf., Cambridge, UK, Sep. 19-22, 1999, [Lecture Notes in Computer Science 1679], Springer, Berlin, DE (XP019036244, ISBN: 978-3-540-66503-8).

Office Action for Japanese Application No. 2019-186976 dated Dec. 1, 2020.

Nam, Denis et al. "Leg-length Inequalities Following THA Based on Surgical Technique", Orthopedics, vol. 36, No. 4, Apr. 1, 2013 (Apr. 1, 2013), pp. e395-e400, XP055737452, US ISSN: 0147-7447, DOI: 10.3928/01477447-20130327-11.

David Larose et al "Post-operative Measurement of Acetabular Cup Position Using X-ray/CT Registration", Feb. 11, 2004, Medical Image Computing and Computer-Asssisted Intervention, (Miccai), International Conference. Proceedings,, pp. 1104-1113, XP019001231, ISBN: 978-3-540-41189-5.

Hofmann A.A. Et Al.: "Minimizing leg-length inequality in total hip arthroplasty; Use of preoperative templating and an intraoperativeX-ray", The American Journal of Orthopedics, vol. 37, No. 1, Jan. 1, 2008 (Jan. 1, 2008), pp. 18-23, XP055624740.

Summons to attend oral proceedings pursuant to Rule 115(1) EPC in European Application No. / Patent No. 15755633.3-1209 / 3113710 dated May 8, 2020.

Summons to attend oral proceedings pursuant to Rule 115(1) EPC in European Application No. / Patent No. 15755633.3-1209 / 3113710 dated Feb. 9, 2021.

Penney G P et al: "Postoperative Calculation of Acetabular Cup Position Using 2-D-3-D Registration", IEEE Transactions on Biomedical Engineering, IEEE Service Center. Piscataway, NJ, USA, vol. 54, No. 7, Jul. 1, 2007 (Jul. 1, 2007), pp. 1342-1348, XP011185541, ISSN: 001 8-9294, DOI: 10.11 09/TBME.2007.890737.

Examination report No. 1 for standard patent application, for Australian Patent Application No. 2016371212 dated Mar. 31, 2021.

"Communication pursuant to Article 94(3) EPC," for EP Application No. 17739110.9-1207 dated Jul. 6, 2021.

Depuy Orthopaedics, Inc., "Corail Total Hip System: Surgical Technique," 2005, 16 pages.

Examination Report No. 1 for Australian Patent Application No. 2017207496 dated Aug. 23, 2021.

"Communication," pursuant to Rule 62 EPC, European Search Report for EP Application No. 21170146.1-1210 dated Jul. 29, 2021.

Le Duff, Michel J. et al., "Benefits of thin-shelled acetabular components for metal-on-metal hip resurfacing arthroplasty," Journal of Orthopaedic Research, v. 28, No. 12, Dec. 1, 2010, p. 1665-1670.

Lu Ming et al., "Reliability and Validity of Measuring Acetabular Component Orientation by Plain Anteroposterior Radiographs," Clinical Orthopaedics and Related Research, v. 471, No. 9, Sep. 1, 2013, p. 2987-2994.

Labronici Pedro José et al: "Positioning of the acetabular component in cemented prostheses—radiographic calculation," Revista Brasileira De Ortopedia (English Edition), v. 48, No. 1, Jan. 1, 2013, p. 62-68.

\* cited by examiner

Analysis Menu

300

302 Operative Side | Left | Right

310 Preoperative Menu

315 Create Pre-Operative Hip Template

318 Add X-Ray

320 Intraoperative Menu

322 Trial Leg Length & Offset Changes

324 Contralateral Overlay

326 Cup Check

328 Surgical Approach
Posterior Approach Selected

FIG. 3

SYSTEM AND METHOD FOR INTRAOPERATIVELY DETERMINING IMAGE ALIGNMENT

FIELD

This application related to the analysis of medical images and more specifically to facilitating medical decision support and guidance intraoperatively.

BACKGROUND

During medical procedures, such as orthopedic surgery, preoperative images may be compared with intra-operative images taken at various points during performance of a medical procedure. Comparison of preoperative and intraoperative images may assist medical personnel in performance of the medical procedure such as by guiding selection, placement, and positioning of surgical implants or other components.

However, relative movement between the patient's position and/or relevant anatomical features of the patient and the imaging apparatus, which can occur during surgery, may result in subtle intraoperative errors. For example, the pose of the imaging apparatus in the preoperative image relative to an anatomical feature of interest may be different from the corresponding relative pose in the intraoperative image, which can lead to incorrect intraoperative decisions. Such intraoperative errors, which may not be detected by conventional systems, may have a significant impact on eventual surgical outcomes. For example, in an orthopedic procedure such as total hip arthroplasty (THA), the positioning of a functional component may be affected, which can result in post-operative complications such as leg length discrepancies, impingement, movement limitations, etc. These post-operative complications may eventually cause premature component failure, component dislocation, affect patient mobility, cause patient pain and/or discomfort, increase recovery time, and/or require additional surgery. Even when potential intraoperative errors resulting from patient movement relative to the imaging apparatus are detected during the medical procedure, such detection typically does not occur until later stages of the medical procedure. Late detection can result in repeating of large portions of the surgical process thereby lengthening operation time, decreasing medical personnel confidence in the system, increasing the cost of procedures, increasing the likelihood of other unrelated errors because of medical personnel fatigue, etc. In addition, even when detected, conventional systems may merely report the discrepancy but provide no further guidance.

Disclosed embodiments facilitate early detection of relative movement between the patient's position and/or relevant anatomical features of the patient and the imaging apparatus, while providing guidance and feedback to correct errors.

SUMMARY

Disclosed embodiments pertain to a method to intraoperatively determine a suitability of an intraoperative image for further intraoperative surgical analysis. The method may comprise: determining, based on at least three pelvic feature points in a pre-operative image, a first angle; determining, based on at least three corresponding pelvic feature points in a first intraoperative image, a corresponding second angle; determining the suitability of the intraoperative image for the further intraoperative surgical analysis based on a comparison of the first angle and the corresponding second angle; and in response to a determination that the first intraoperative image is not suitable for the intraoperative surgical analysis, providing an indication of a movement direction for a fluoroscopy camera used to obtain the first intraoperative image.

In another aspect, an apparatus may comprise: a communications interface to receive a first intraoperative image captured by a fluoroscopy camera, a memory capable of storing a preoperative image and the first intraoperative image, and a processor coupled to the memory and the communications interface. In some embodiments, the processor may be configured to: determine, based on at least three pelvic feature points in the pre-operative image, a first angle; determine, based on at least three corresponding pelvic feature points in the first intraoperative image, a corresponding second angle; determine the suitability of the intraoperative image for further intraoperative surgical analysis based on a comparison of the first angle and the corresponding second angle; and in response to a determination that the first intraoperative image is not suitable for the intraoperative surgical analysis, provide an indication of a movement direction for the fluoroscopy camera used to obtain the first intraoperative image.

Disclosed embodiments also pertain to means for determining, based on at least three pelvic feature points in a pre-operative image, a first angle; means for determining, based on at least three corresponding pelvic feature points in a first intraoperative image, a corresponding second angle; means for determining the suitability of the intraoperative image for the further intraoperative surgical analysis based on a comparison of the first angle and the corresponding second angle; and in response to a determination that the first intraoperative image is not suitable for the intraoperative surgical analysis, means for providing an indication of a movement direction for fluoroscopy means used to obtain the first intraoperative image.

In a further aspect, a non-transitory computer-readable medium may comprise instructions to configure a processor to: determine, based on at least three pelvic feature points in a pre-operative image, a first angle; determine, based on at least three corresponding pelvic feature points in a first intraoperative image, a corresponding second angle; determine the suitability of the intraoperative image for further intraoperative surgical analysis based on a comparison of the first angle and the corresponding second angle; and in response to a determination that the first intraoperative image is not suitable for the intraoperative surgical analysis, provide an indication of a movement direction for the fluoroscopy camera used to obtain the first intraoperative image.

BRIEF DESCRIPTION OF THE DRAWINGS

FIG. 3 shows a representation of a Graphical User Interface (GUI) menu presented to a user for intraoperative analysis.

Figure 1A:
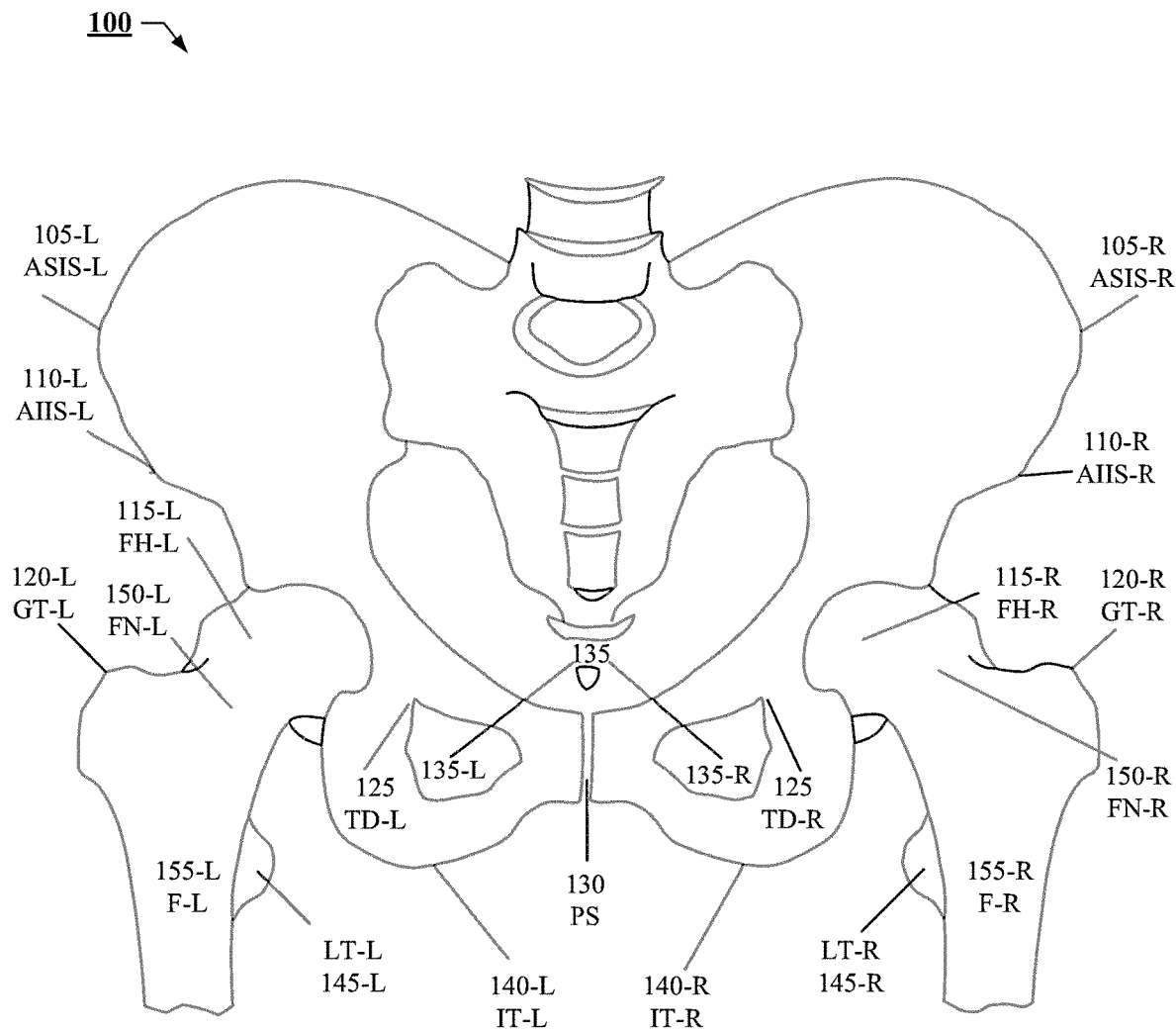
FIG. 1A is a schematic image of a frontal view of a pelvic girdle of a patient illustrating various pelvic anatomical features.

Identical labels and/or reference numerals in different figures refer to the same element. Different instances of a common element type may be indicated by appending a label for the common element with an additional label. For example, different instances of femoral neck FN 150 may be labeled FN-R 150-R (for the right femoral neck) and FN-L 150-L (for the left femoral neck). Unless noted otherwise, operations applicable to an instance of the common element (e.g. right "R") may also be applicable to another instance of the common element (e.g. left "L"). For example, the figures show the right side of the hip to illustrate techniques used herein, it is understood that the techniques are also applicable (with appropriate modifications) to the left side of the hip.

References may also be made to the common element without an extra appended label (e.g. FN 150), which may refer to the element generically and/or to any instance of the element.

In some instances, additional numeric suffixes (e.g. 1, 2 . . . N) may be appended to the label/reference numeral used for the common element. For example, when comparing a first and second image, an additional suffix (e.g. "-1" or "-2") may be added to distinguish between elements ("-1") in the first image from corresponding elements ("-2") in the second image.

DETAILED DESCRIPTION

Disclosed embodiments facilitate intraoperative image analysis and provide decision support during medical procedures such as orthopedic surgery. In some embodiments, the methods disclosed may be applied during orthopedic surgery of the hip, including during Total Hip Arthroplasty (THA). The term arthroplasty refers to a surgical procedure that restores joint function. In some instances, a prosthesis or implant may be used during arthroplasty. In THA, the acetabulum and femoral head can both be replaced, while in hip hemi-arthroplasty (HHA), the femoral head is typically replaced. Although, hip arthroplasty is used an example to illustrate embodiments herein, the techniques and systems disclosed may also be applied to other medical procedures including arthroscopy of the knee, arthroscopy of the wrist, etc. Moreover, although human subjects are used in the descriptions herein, the techniques and systems disclosed may also be applied to non-human subjects with appropriate modifications. As used herein, the term hip arthroplasty includes various surgical approaches including the posterior approach, direct lateral approach, and direct anterior approach. In the anterior approach, surgery is performed from an incision at the front of the hip, while, in the posterior approach, surgery is performed using an incision at the back of the hip. In the direct lateral approach, an incision is made at the side of the hip.

When performing arthroplasty, fluoroscopic evaluation of the patient is often performed using an anterior-posterior (AP) image, which is taken from the front toward the back. The fluoroscopy image may be taken, for example, with a C-arm imaging apparatus, where a C-shaped arm is used to couple the radio source (e.g. X-ray) to the radiographic detector. C-arms may also be coupled to a display, which may facilitate viewing of high-resolution X-ray images in real time. Medical personnel may view images, monitor progress, and take appropriate action based on the images. The C-arm can be moved and repositioned during surgery to focus on various areas of interest and/or to obtain new images of a current area of interest.

During surgery, there may be relative movement between the position of the patient (and/or patient anatomical features of interest) relative to the fluoroscopy source. For example, during THA using the posterior approach, motion of the patient's pelvis may occur. Thus, relevant sections of intra-operative images (e.g. subsequent to the motion of the pelvis) may not correspond, in some respects, when compared to a preoperative image being used for intraoperative analysis. The differences between the preoperative and intra-operative images may be subtle and may not be immediately apparent to the surgeon and/or other medical personnel. For example, the relative pose of the imaging apparatus in the preoperative image may be different from the corresponding relative pose in the intra-operative image, which can lead to incorrect intraoperative decisions. The term relative pose is used to refer to position and orientation of imaging source relative to an anatomical feature of interest. Pose may be described, for example, using positional coordinates (x, y, z) and angular coordinates ($\phi$, $\theta$, $\psi$) (which may describe roll, pitch, and yaw, respectively) relative to a frame of reference. In some instances, the frame of reference may be centered on an anatomical feature of interest.

As outlined previously, if relevant differences (e.g. due to relative pelvic motion) between the preoperative and intra-operative images go undetected, then, intraoperative analysis based on the preoperative and intraoperative images may be incorrect and post-operative outcomes may be negatively impacted.

On the other hand, if the relevant differences between the preoperative and intraoperative images are detected at a late stage of the operation after several intermediate steps have occurred, then, conventionally: (a) intraoperative images are retaken after the C-arm is repositioned; (b) intermediate steps are repeated, and (c) the intraoperative analysis is performed again. Steps (a) through (c) are repeated until the intraoperative image is determined to be acceptable, which may involve several iterations. As outlined above, the later detection and procedural repetition can increase the length of the procedure, increase the likelihood of mistakes, increase cost, etc. Moreover, the resulting complexity results in decreased adoption of computer-assisted tools, even when the tools may deliver better outcomes overall.

Thus, some disclosed embodiments facilitate intraoperative image analysis early in the surgical process thereby facilitating prompt determination of intraoperative image discrepancies. In some embodiments, the early determination of any intraoperative image discrepancies may occur prior to determination of biomechanical parameters and/or further analysis based on the preoperative and intraoperative images. Some disclosed embodiments also provide decision support and guidance during to medical personnel including related to C-arm positioning/re-positioning. In some embodiments, information pertaining to positional discrepancies identified in the intraoperative image may be provided to the imaging apparatus and/or to a computer or control system associated with the imaging apparatus.

FIG. 1A is a schematic image of a frontal view of a pelvic girdle 100 of a patient illustrating various pelvic anatomical features. PG 100 may also be referred to as the pelvis or hip. Pelvic anatomical features may also be referred to herein as pelvic feature points, pelvic landmarks, or anatomical landmarks. In some embodiments, the anatomical features may be identified in a first image (e.g. a preoperative image) and in a second image (e.g. an intraoperative image). Two or more feature points may also be joined to form a line (e.g. such as a reference line or axis), or curve, or other geometrical shape (e.g. delineating some anatomical feature), and/or other descriptors, which may be used during image registration. Accordingly, image registration techniques based on the locations of the feature points and/or other descriptors may be used to align the first and second images. Registration may involve one or more of scaling, rotation, and translation. In some embodiments, the identification of feature points may be automatic. In some embodiments, the identification of feature points may be computer-assisted. Further, users may be provided with options to confirm and/or adjust the location of feature points in images prior to registration.

In FIG. 1A, for example, the obdurator foramen (OF) 135 (e.g. right obturator foramen OF-R 135-R and left obturator foramen OF-L 135-L) and pubic symphysis PS 130 are shown. For the purposes of the description below the lower corner of PS 130 is referred to as the inferior PS and the upper corner is referred to as the superior PS. OF 135 and PS 130 in two distinct images may serve as reference points and/or descriptors for image comparison and/or image registration. Various other example anatomical features are also shown in FIG. 1, which may be used as pelvic reference points and/or descriptors. The features outlined in FIG. 1 are merely examples and other pelvic features may also be used to practice one or more of the techniques disclosed herein. In some instances, in FIG. 1, for simplicity and ease of description, only the right or left feature point has shown.

FIG. 1A also shows femur F 155 (right femur F-R 155-R and left femur F-L 150-L) with: (a) femoral head FH 115 (right femoral head FH-R 115-R and left femoral head FH-L 115-L); (b) femoral neck FN 150 (right femoral neck FN-R 150-R and left femoral neck FN-L 150-L, respectively); (c) greater trochanter GT 120 (right greater trochanter GT-R 120-R and left greater trochanter GT-L 120-L); and (d) lesser trochanter LT 145 (right lesser trochanter LT-R 145-R and left lesser trochanter LT-L 145-L, respectively).

Left femoral head FH-L 115-L engages the left acetabulum of pelvic girdle PG 100, while right femoral head FH-R 115-R engages the right acetabulum of PG 100. Also shown in FIG. 1 are: ischial tuberosities IT 140 (right ischial tuberosity IT-R 140-R and left ischial tuberosity IT-L 140-L) at the bottom of the ischium, "teardrops" TD 125 (right teardrop TD-R 125-R and left teardrop TD 125-L), which are radiological features relating to a bony ridge along the floor of the acetabular fossa, and the anterior superior iliac spine ASIS 110 (right ASIS ASIS-R 110-R and left ASIS ASIS-L 110-L), the anterior inferior iliac spine AIIS 105 (right AIIS AIIS-R 105-R and left AIIS AIIS-L 105-L) of the ileum.

Similarly, when techniques described herein are applied to other parts of the anatomy, other appropriate features may be used. For example, carpal bones may serve as a stationary base in images for radial bone fixation and other wrist-related procedures. In general, any relatively stationary anatomical feature associated with a patient may be used for a stationary base (as opposed to a mobile feature that may be positioned differently in two or more images).

In some instances, a longer stationary base may be selected over a shorter stationary base, because the longer base may increase accuracy of image overlays and facilitate more accurate image scaling. In addition, stationary bases closer to the area of anatomical interest are preferable to reduce the risk of parallax-induced error. For example, if the area of interest is the hip joint, then the ideal stationary base will be near the hip.

Figure 1B:
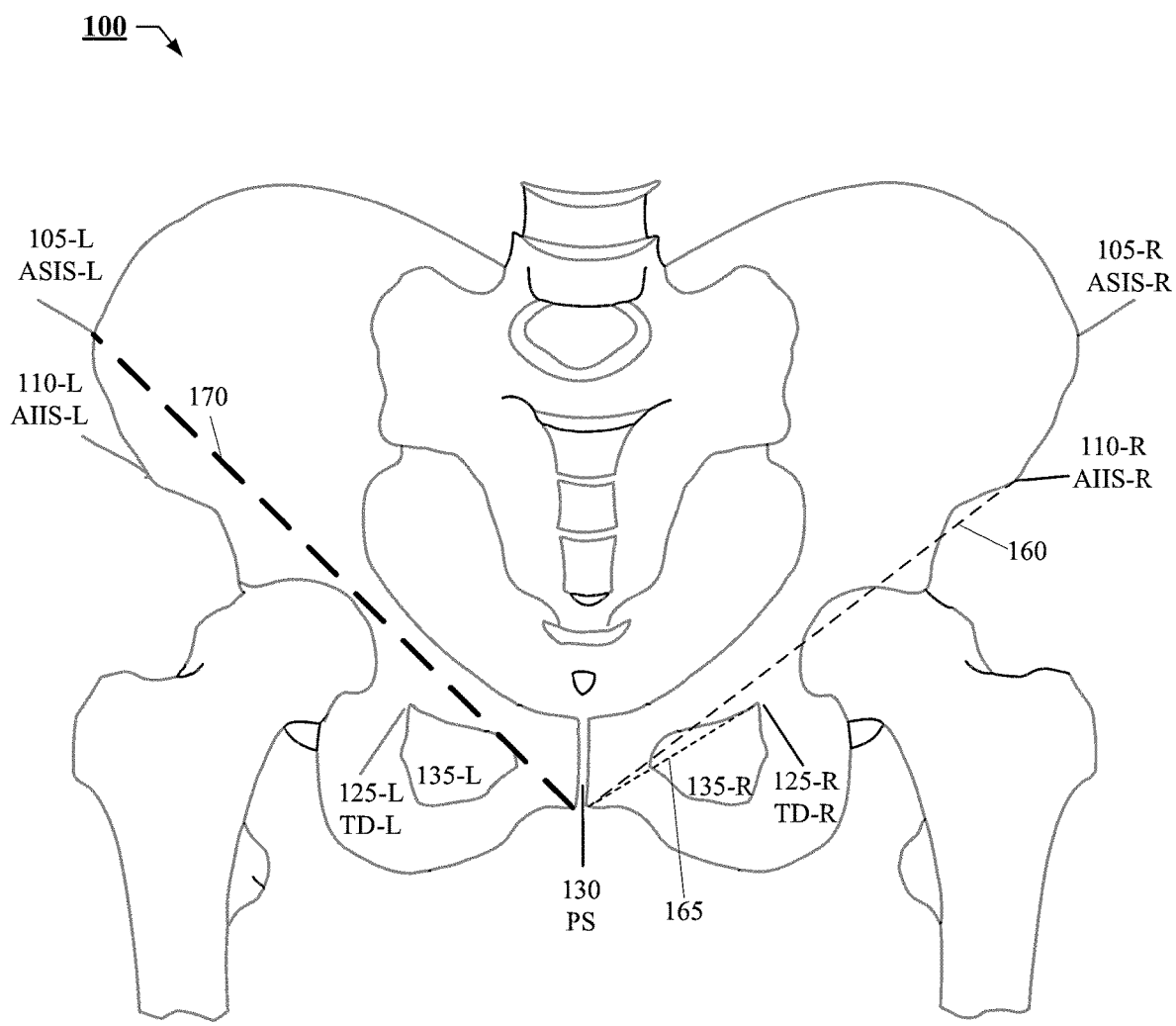
FIG. 1B, shows various example pelvic reference lines, or pelvic axes, which may be used to establish base lines to facilitate hip arthroplasty.

As shown in FIG. 1B, in some procedures involving hip surgery, for example, various pelvic reference lines, or pelvic axes, may be used to establish base lines. For example, as shown in FIG. 1B, (i) a first pelvic reference line 165 may be a stationary base line that begins at the inferior pubic symphysis PS 130, touches or intersects at least a portion of an obturator foramen OF (e.g. OF-R 135-R), and extends to the "teardrop" TD (e.g. TD-R 125-R); or, (ii) a second pelvic reference line may be a stationary base line 160 that begins at the inferior pubic symphysis PS 130, touches or intersects at least a portion of an obturator foramen OF (e.g. OF-R 135-R), and extends to the anterior interior iliac spine AIIS 110 (e.g. ASIS-R 110-R); or, (iii) a third pelvic reference line may be a stationary base line 170 that begins at the inferior pubic symphysis PS 130 and extends to the anterior superior iliac spine ASIS 105 (e.g. ASIS-L 105-L). In general, any two feature points such as two identifiable anatomical features, or two locations on a single anatomical feature may be used to establish a stationary reference line or axis. In some embodiments, curves, shapes, and/or other non-linear stationary reference lines may be used. For example, additional anatomical feature points may be identified and used to establish non-linear bases.

In some embodiments, one or more additional identifiable anatomic feature points or landmarks (or a set of landmarks) separate from the reference lines described above may be identified. These additional landmarks may be also be stationary and lie on or close to the area of anatomical interest. The additional landmarks may be used, in some instances, to analyze the accuracy of image overlays. For example, the inferior portion of the ischial tuberosity IT 140 can be identified as an additional landmark. This landmark, in conjunction with the stationary base or reference line, may be used to detect any differences or errors in pelvic anatomy or the overlay, which will enable the physician to validate, or to have more confidence in, the output of the present system.

In some embodiments described herein, angular information between two reference lines may be used to determine a likelihood of suitability of an intraoperative image for comparison and/or overlay with a preoperative image; and/or to determine a likelihood of suitability of an intraoperative image for intraoperative analysis (e.g. in relation to the estimation of various anatomical and biomechanical parameters intraoperatively). The intraoperative analysis may be used to: select trial prosthetic(s), position and orient the trial prosthetic(s), and determine anatomical and biomechanical parameters based on the placement (position and/or orientation) of the selected trial prosthetic(s).

The term "trial hip prosthetic" is utilized herein to designate an initial implant selected by a surgeon as a first medical device to insert at the surgical site, which is either the right side or the left side of a patient's hip in this construction. In some techniques, the trial prosthetic may be selected based on initial digital templating in a manner similar to the procedure described in relation to FIG. 2 below.

Figure 2:
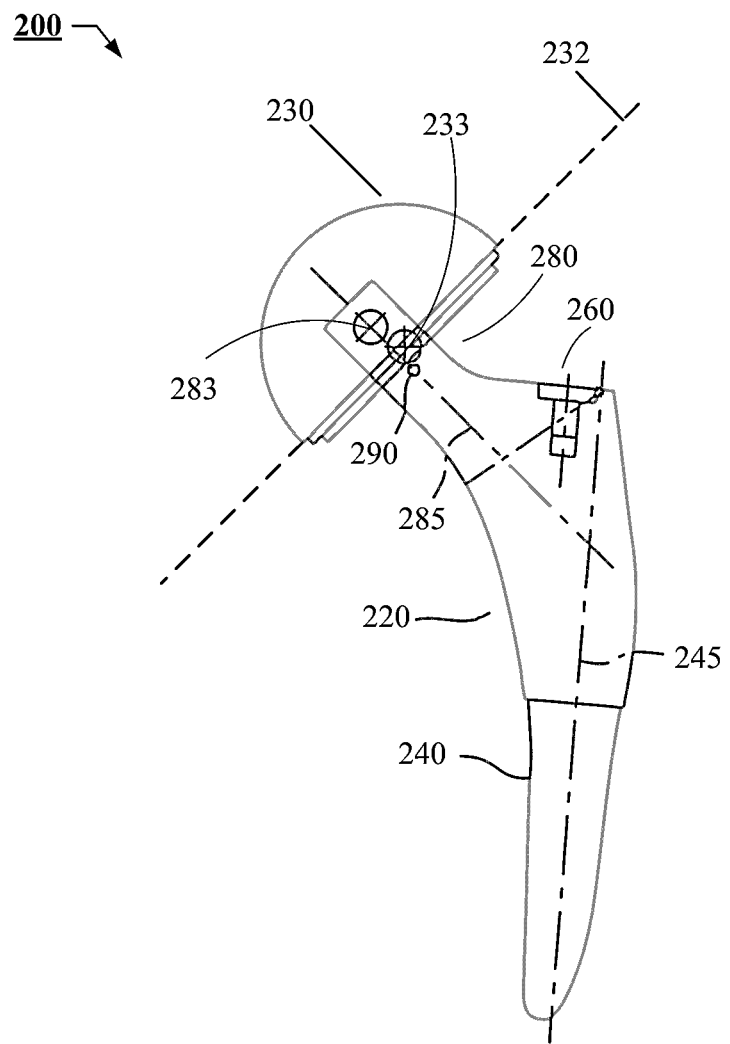
FIG. 2 is a schematic image depicting a template image of a hip prosthesis.

FIG. 2 is a schematic image depicting a hip prosthesis 200. Hip prosthesis 200 includes femoral prosthesis component 220, which further includes femoral stem 240, a fastener recess 260, a support 280 with a trunion 290, and an acetabular component 230 carried by the support 280. Dashed line 285 indicates the longitudinal axis of support 280 and dashed line 245 indicates a longitudinal body axis for hip prosthesis 200 to be aligned relative to a longitudinal axis of the femur F 155 (e.g. F-L 150-L not shown in FIG. 2), as described further herein. Also shown are a center of rotation 283 for support 280 of femoral body component 220 and a center of rotation 233 for acetabular component 230.

Centers of rotation 233 and 283 (associated with hip prosthesis template image 200) may be used to determine anatomical and/or biomechanical parameters such as an offset parameter and/or a leg length differential parameter. Determination of these and other parameters is discussed in U.S. patent application Ser. No. 14/974,225 filed 18 Dec. 2015 (now U.S. Pat. No. 10,433,914), which is a continuation-in-part application of U.S. patent application Ser. No. 14/630,300 filed 24 Feb. 2015 (now U.S. Pat. No. 10,758,198), which claims priority to U.S. Provisional Application No. 61/944,520 filed 25 Feb. 2014, U.S. Provisional Application No. 61/948,534 filed 5 Mar. 2014, U.S. Provisional Application No. 61/980,659 filed 17 Apr. 2014, U.S. Provisional Application No. 62/016,483 filed 24 Jun. 2014, U.S. Provisional Application No. 62/051,238 filed 16 Sep. 2014, U.S. Provisional Application No. 62/080,953 filed 17 Nov. 2014, and U.S. Provisional Application No. 62/105,183 filed 19 Jan. 2015. All of the above applications are incorporated by reference herein in their entireties.

In some embodiments, a digital template image of hip prosthesis 200 may be generated based on user selected or entered parameters such as size, type, etc. The digital template image of hip prosthesis 200 may be superimposed over a preoperative and/or a suitable intraoperative image and aligned appropriately. In some embodiments, the preoperative and/or intraoperative images may then be analyzed intraoperatively to determine various anatomical and/or biomechanical parameters prior to final implantation of the prosthetic. In the description below, labels and reference characters from FIG. 2 are used to refer to components of hip prosthesis 200 (whether in the form of a digital template, a trial prosthesis, or a final prosthesis).

FIG. 3 shows a representation of an example Graphical User Interface (GUI) 300 presented to a user for intraoperative analysis.

As shown in FIG. 3, GUI 300 provides Operative Side selection 302 for the user to select an operative side (left or right). In some embodiments, selection of an operative side (left or right) may automatically cause appropriate (left or right) digital image templates to be loaded.

Preoperative menu 310, which may be invoked preoperatively and/or intraoperatively, may facilitate preoperative planning (e.g. when invoked preoperatively) and/or the retrieval of stored preoperative images, templates, and/or other analytics (e.g. when invoked intraoperatively). For example, selecting Create Preoperative Hip Template creation 315 may facilitate creation of preoperative hip templates (e.g. using hip prosthesis template image 200), associating and/or aligning hip prosthesis template images 200 with preoperative images. In some embodiments, selecting Add X-Ray 318 may facilitate the importing, storing, and/or addition of preoperative images and/or preoperative templates and/or other preoperative analytics associated with a patient.

In some embodiments, GUI 300 may be part of a computer program running on a local computer or computer subsystem with locally stored images (e.g. proximate to where the medical procedure is being performed—such as the same or nearby room). In other situations, some portions of the computer program associated with GUI 300 may be run on a local remote server (e.g. within the medical facility where the medical procedure is being performed) or a remote server (e.g. such as a private cloud). In some embodiments, a hybrid approach may be used, where one more tasks are performed locally (e.g. on a local computer) during a medical procedure, whereas other tasks (preoperative and/or post-operative) may be performed remotely with synchronization (e.g. exchange of stored images and/or other medical records) between the local and remote computers occurring prior to the start of the medical procedure. A hybrid system where intraoperative functions are local may prevent issues arising from temporary network and/or other outages.

Intraoperative menu 320, which may be invoked intraoperatively, may comprise selections for Trial Length and Offset Changes 322, Contralateral Overlay 324, Cup Check 326, and Surgical Approach 328 (e.g. anterior, posterior, lateral, etc.). FIG. 3 shows selection of Posterior Surgical Approach 328 has been selected. In some embodiments, program components Trial Length and Offset Changes 322, Contralateral Overlay 324, Cup Check 326, etc. may offer analytics tailored to the selected Surgical Approach 328.

In some embodiments, selecting Trial Length and Offset Changes 322 may invoke program functionality to compare a pre-operative or intra-operative X-ray-type image of a patient's anatomy with an initial intra-operative X-ray-type image of a trial prosthesis, In some embodiments, selection of Trial Length and Offset Changes 322 may also invoke program functionality to select a trial (or final) prosthetic using hip prosthesis template image 200 (in FIG. 2), and determine likely changes of offset and/or leg length to help guide surgical decision making.

In some embodiments, selecting Contralateral Overlay 324 may invoke program functionality to compare a contralateral pre-operative X-ray-type image of a patient's anatomy with an initial intra-operative X-ray-type image of a trial prosthesis. For example, in some situations, an ipsilateral hip may have degenerated (e.g. due to disease and/or injury) so a contralateral hip image may be used instead of the ipsilateral hip image. Accordingly, in the example above, the contralateral image may be flipped and overlaid to determine bone and implant alignment between images, perform feature matching between the images, and/or analyze offset, length differential and orientation of at least one of a bone and an implant within the images. In other situations, contralateral overlay 324 may invoke functionality to depict the extent of any differences and/or changes to pelvic anatomy (e.g. between the ipsilateral and contralateral hip). Thus, the contralateral overlay may provide additional surgical decision support and validation.

In some embodiments, selecting Cup Check 326 may invoke program functionality to perform anteversion and abduction analysis related to an acetabular component (e.g. a trial acetabular cup, a standard acetabular cup, a reamer, etc.) selected by a surgeon. In some embodiments, Cup Check 326 may invoke program functionality to determine biomechanical parameters such as anteversion of a reconstructed AP Pelvis, abduction angle, or inclination, etc.

Hip anteversion refers to the inward rotation of the femur. Anteversion may be calculated based on the rotation of the acetabular component. As one example, anteversion may be understood as the angle in the sagittal plane between the acetabular axis and the (assumed) longitudinal axis of the patient. The acetabular axis is a line passing through the center of socket (or acetabular component) and perpendicular to plane of the socket face (or plane of the acetabular component e.g. acetabular component plane 232 in FIG. 2). In some embodiments, Cup Check 326 may invoke program functionality to determine anteversion radiographically based on identified features in intra-operative images.

Hip abduction refers to the movement of the hip joint as the leg is moved away from the longitudinal of the body. Abduction angle or inclination may be understood as the angle between the acetabular axis and the horizontal plane (e.g. parallel to the floor). Cup Check 326 may invoke program functionality to determine abduction angle radiographically based on identified features in intra-operative images.

The use of digital templating techniques can assist surgical decision making and significantly improve medical outcomes. However, as outlined previously, imaging source pose changes relative to anatomical features can affect the analysis. Therefore, determination of suitable images prior to running exhaustive trials and/or analytics, overlay analysis, etc. can provide timely determination of image usability for analytic tools and thereby potentially decrease medical procedure time. In some embodiments, disclosed techniques may be run initially (e.g. upon selection of surgical approach 328 using selected preoperative images and may be triggered by an acquisition of a new intraoperative image) to determine suitability of the acquired intraoperative image for intraoperative analysis. In some embodiments, disclosed techniques may be run (e.g. once surgical approach 328 and a preoperative image has been selected and intraoperative image has been captured) prior to performing intraoperative analysis by one or more of Trial Length and Offset Changes 322, Contralateral Overlay 324, Cup Check 326, or other functional components. Performing preliminary determination of image suitability may decrease the likelihood imaging device relative pose-change related errors during the above steps.

Figure 4:
FIG. 4 is an example preoperative fluoroscopic image of a portion of the pelvic girdle of a patient illustrating some anatomical features.

FIG. 4 is an example GUI 400 displaying preoperative fluoroscopic image 430 of a portion of the pelvic girdle of a patient illustrating some anatomical features. In some embodiments, preoperative fluoroscopic image 400 may be obtained and/or displayed by selecting an appropriate stored image (e.g. using functionality provided by Add X-Ray 318 in GUI 300 in FIG. 3). In some embodiments, a program may display GUIs 410, 430, and 440 during image capture and/or for evaluation/confirmation subsequent to capture.

In some embodiments, GUI 410 may provide a description of the image being shown (e.g. based on functionality that was active when the preoperative image was captured) and/or appropriate annotations by medical personnel. For example, GUI 410 describes the image shown in window 420 as an "X-Ray of ipsilateral hip Anterior-Posterior (AP) Hip prior to neck cut." In some embodiments, an operator may be asked to select the type of image (e.g. "AP Hip") and parameters associated with the image (e.g. "prior to neck cut") at the time of image capture.

FIG. 4 shows example anatomical features such as PS 130, GT-R 120-R, and a section of the pelvic bone (PB) above the acetabulum (shown as PB-R 420-R in FIG. 4) that may have been automatically identified in the preoperative image. In some embodiments, a user may be asked to confirm identified features, and/or locate/relocate the identified features (e.g. PS 130, GT-R 120-R, and PB 420).

In addition, Tips window 440 may include information for proper image capture and/or image evaluation by medical/radiological personnel such as asking a user to "Center [the] acetabulum on screen", confirm that the "Greater trochanter, femoral diaphysis, pubic symphysis, & pelvic bone above acetabulum [are] shown," in the image, and (e.g. when capturing an image of a patient's hip) to ensure that the patient's "leg [is placed] in 10 Degrees of internal rotation and [that the] C-arm [is rainbowed] 10 Degrees over the top to show patient's true offset." Tips window 440 and example anatomical features shown in FIG. 4 are merely examples to illustrate operation and the tips shown and/or features identified in FIG. 4 may vary depending on the type (e.g. Total Hip Arthroplasty (THA)) and/or sub-type (e.g. "Posterior Approach") of medical procedure.

Figure 5:
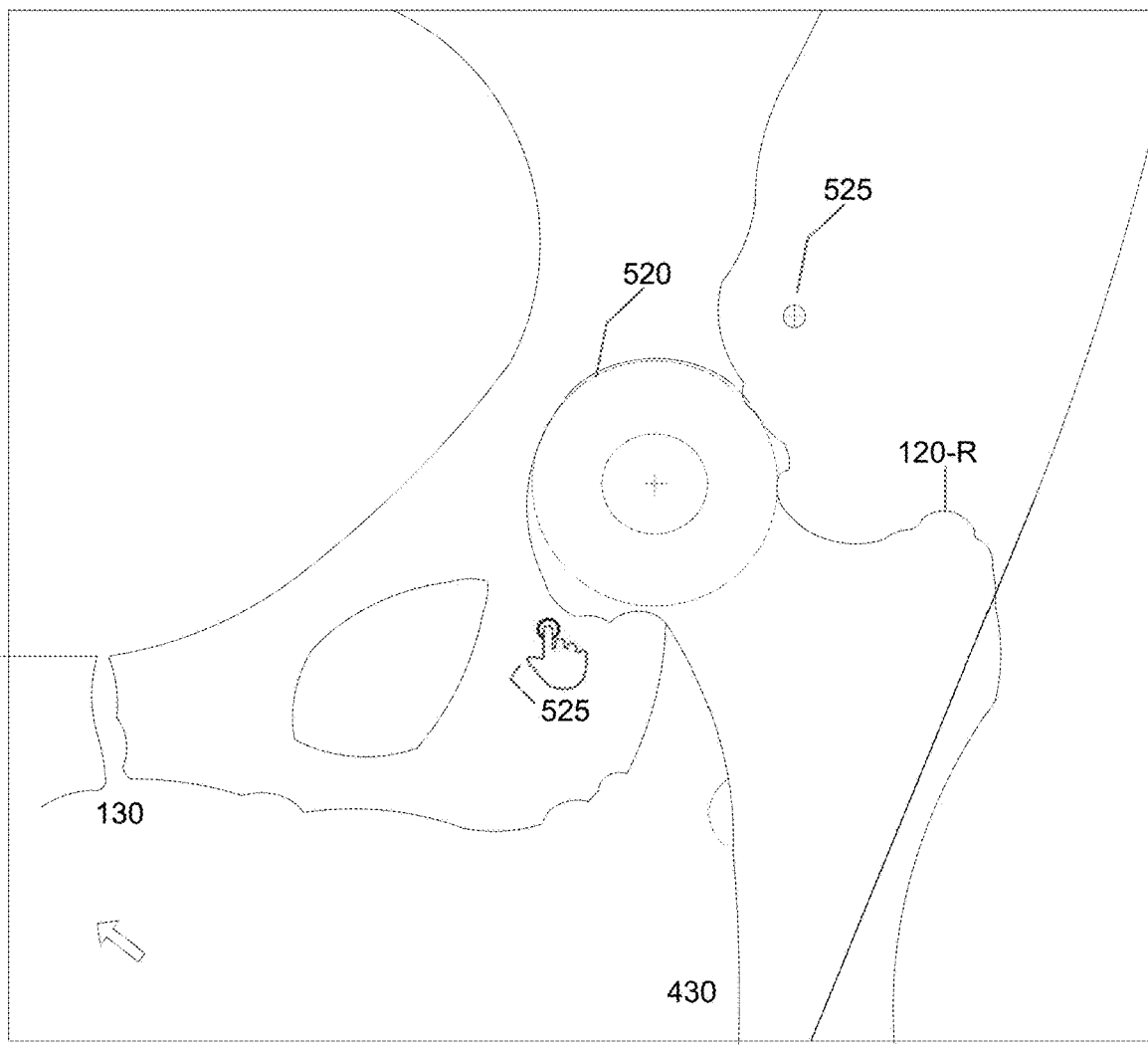
FIG. 5 shows an example displayed fluoroscopic image illustrating a circle drawn around the femoral head in accordance with certain disclosed embodiments.

FIG. 5 shows an example GUI 500 displaying fluoroscopic image 430 illustrating a circle 520 drawn around the femoral head in accordance with certain disclosed embodiments. GUI 500 displays the current operation shown as "Draw Circle around Femoral Head" in window 510. In some embodiments, circle 520 may be placed automatically based on feature points in fluoroscopic image 430. In some embodiments, the program may include functionality to facilitate user adjustment of the size and position of circle 520. GUI 500 may include guide dots 525 to facilitate navigation and/or repositioning of circle 520. Circle 520 may be used (e.g. in a suitable digitally calibrated radiographic image at an appropriate stage) to estimate a size of a final or trial acetabular component 230. In some embodiments, GUI 500 may also show one or more feature points such as PS 130, GT-R 120-R, etc. In FIGS. 5-12B, the feature points shown and information displayed (e.g. tips, guides, etc.) may be based on one or more of program settings, a user profile, and/or a patient profile.

Figure 6:
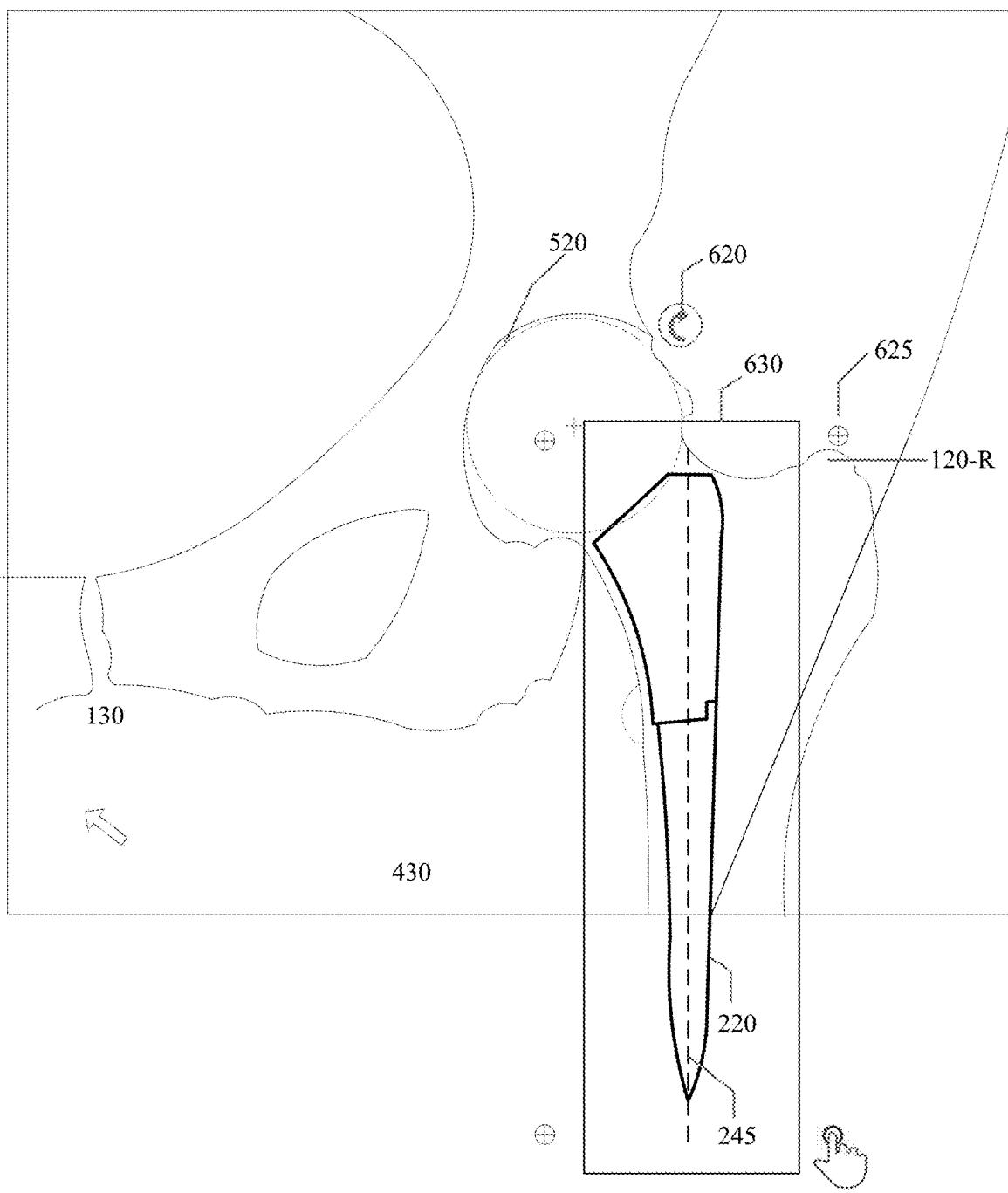
FIG. 6 shows an example displayed fluoroscopic image depicting a digital prosthesis template being aligned with the femoral axis in accordance with certain disclosed embodiments.

FIG. 6 shows an example GUI 600 displaying fluoroscopic image 430 showing digital femoral prosthesis template 220 being aligned with the femoral axis using femoral axis tool 630 in accordance with certain disclosed embodiments. GUI 600 displays the current operation shown as "Align Femoral Axis Tool in Canal" in window 610. In some embodiments, femoral axis tool 630 may be placed and aligned automatically based on feature points in fluoroscopic image 430. In some embodiments, the program may include functionality to facilitate user adjustment of the size, position, and alignment of femoral axis tool 630. GUI 600 may include guide dots 625 to facilitate navigation and/or repositioning of femoral axis tool 630. Femoral axis tool 630 may be associated with digital femoral prosthesis template 220, which may include digital femoral template axis 245 to facilitate alignment of digital femoral prosthesis template 220 with the femur. Rotational adjustments to alignment may be performed using rotate tool 620. GUI 600 also shows circle 520 as centered in the acetabulum, as well as previously identified feature points PS 130, GT-R 120-R, etc.

Figure 7:
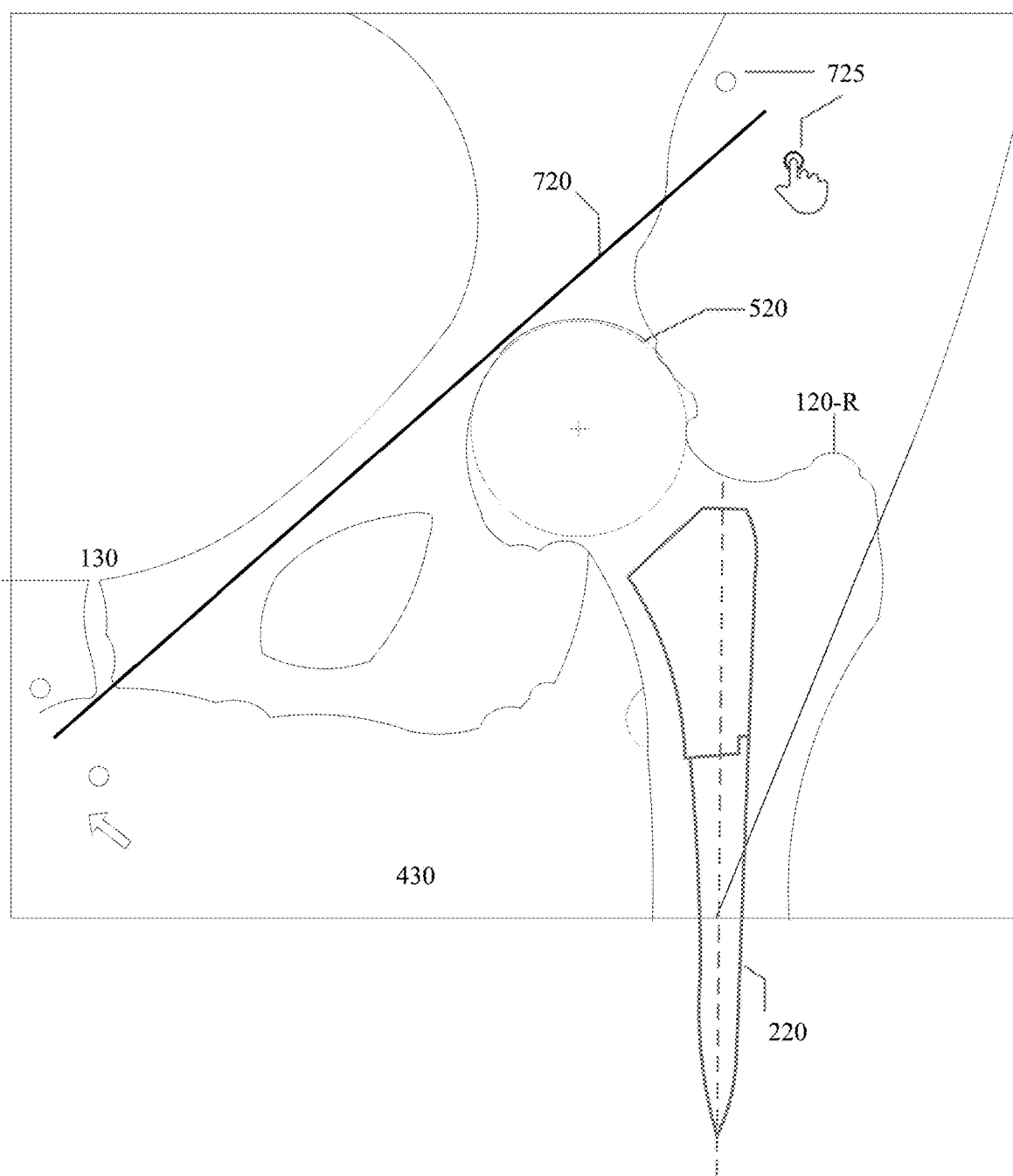
FIG. 7 shows an example displayed fluoroscopic image depicting a pelvic reference line drawn between anatomical features in accordance with certain disclosed embodiments.

FIG. 7 shows an example GUI 700 displaying fluoroscopic image 430 with pelvic reference line 720 drawn between anatomical features in accordance with certain disclosed embodiments. GUI 700 displays the current operation shown as "Mark Pelvic Reference Line" in window 710. In some embodiments, pelvic reference line 720 may be placed automatically based on feature points in fluoroscopic image 430. In some embodiments, the program may include functionality to facilitate user adjustment of the position of pelvic reference line 720. GUI 700 may include guide dots 725 to facilitate navigation and/or repositioning of pelvic reference line 720. Pelvic reference line 720 may correspond, for example, to one pelvic reference lines 160, 165, or 170 (e.g. shown in FIG. 1B). For example, pelvic reference line 720 may correspond to reference line 170 (FIG. 1B) and begin at the inferior pubic symphysis PS 130 and extend to the right anterior superior iliac spine ASIS-R 105-R (not shown in FIG. 7). In some embodiments, pelvic reference line 720 may serve as a base line to facilitate image comparison and/or image registration. GUI 700 also shows now aligned digital femoral prosthesis template 220, circle 520 as centered in the acetabulum, as well as previously identified feature points PS 130, GT-R 120-R, etc.

Figure 8:
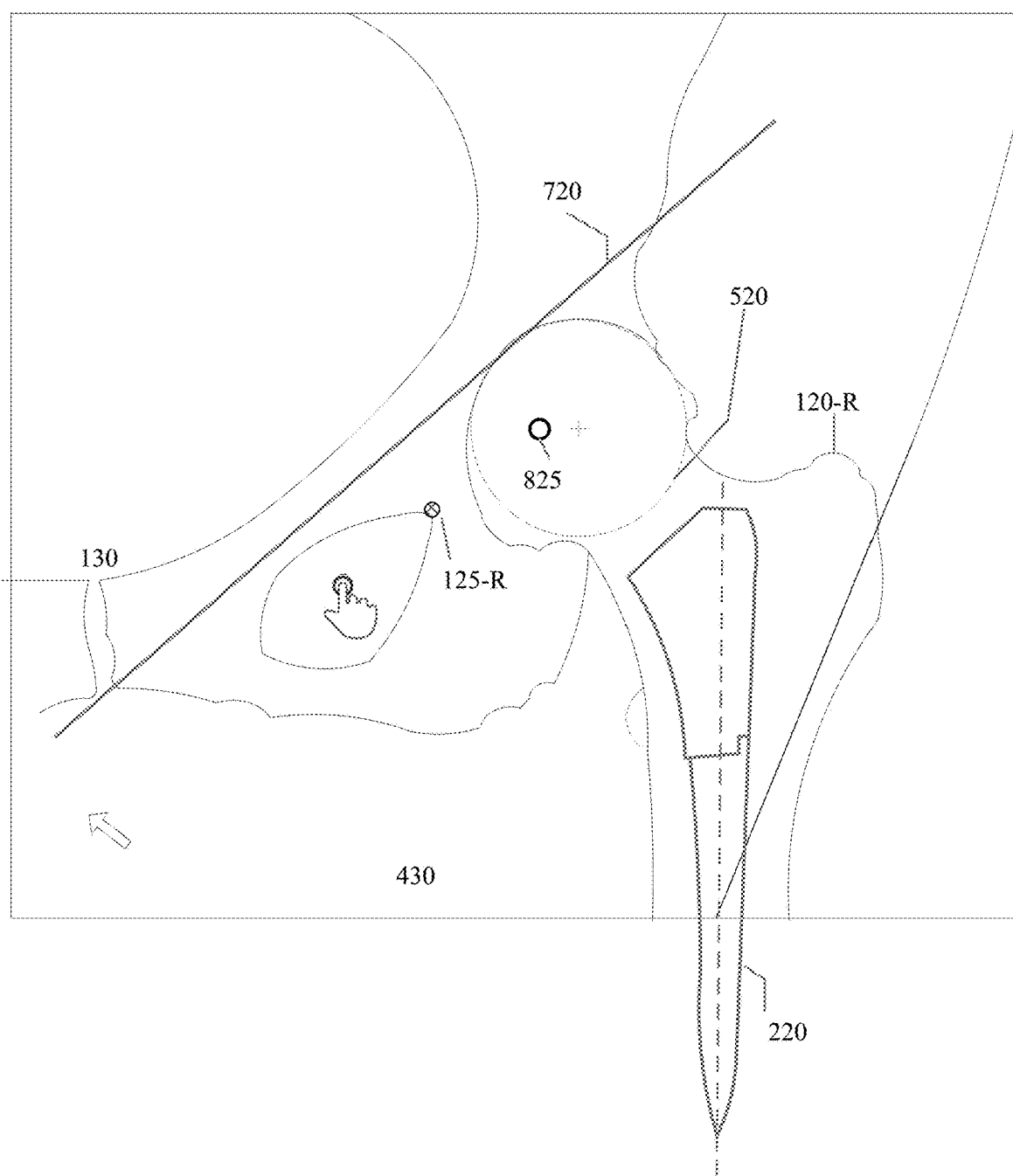
FIG. 8 shows an example displayed fluoroscopic image depicting marking of the pelvic teardrop radiographical feature in accordance with certain disclosed embodiments.

FIG. 8 shows an example an example GUI 800 displaying fluoroscopic image 430 depicting the marking of the pelvic teardrop radiographical feature TD 125. FIG. 8 shows the right pelvic teardrop radiographical feature TD-R 125-R. GUI 800 displays the current operation shown as "Mark Teardrop" in window 810. In some embodiments, TD-R 125-R may be determined automatically based on feature points in fluoroscopic image 430. In some embodiments, the program may include functionality to facilitate user adjustment of the position of TD-R 125-R. GUI 800 may include guide dots 825 to facilitate navigation and/or repositioning of TD-R 125-R in FIG. 8. GUI 800 also shows pelvic reference line 720, aligned digital femoral prosthesis template 220, circle 520 as centered in the acetabulum, as well as previously identified feature points PS 130, GT-R 120-R, etc.

Figure 9:
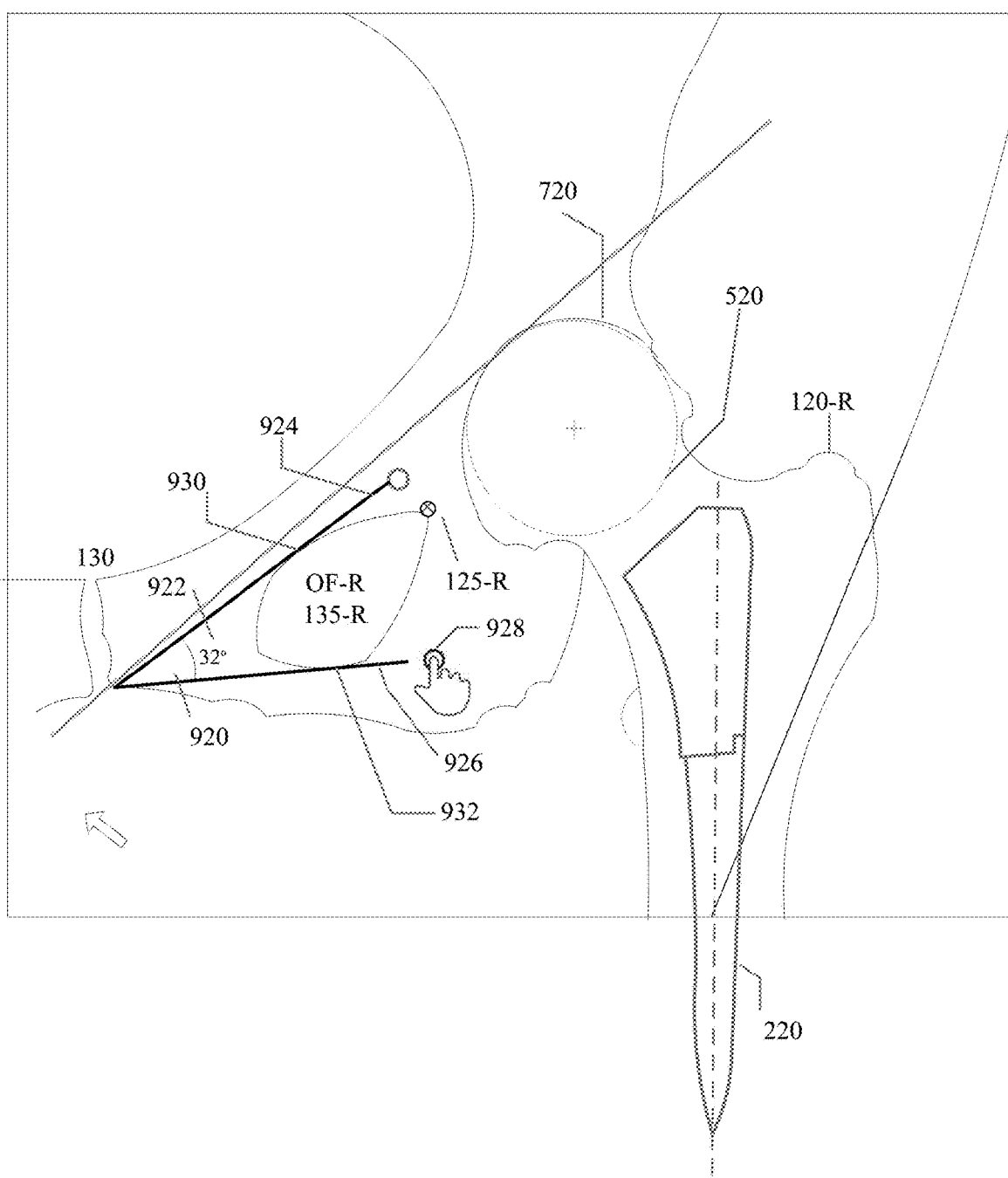
FIG. 9 shows an example displayed fluoroscopic image depicting marking of an obturator angle in accordance with certain disclosed embodiments.

FIG. 9 shows an example GUI 900 displaying fluoroscopic image 430 depicting the marking of an obturator angle 920 in accordance with certain disclosed embodiments. GUI 900 displays the current operation shown as "Mark Obturator Angle" in window 910.

In some embodiments, obturator angle 920 may be formed by the intersection of a upper reference line 924 from the inferior pubic symphysis (PS) 130 to an upper feature point 930 on the upper boundary of OF-R 135-R in preoperative image 430 and a lower reference line 926 from the inferior PS 130 to a lower feature point 932 on the lower boundary of the OF-R 135-R in AP preoperative image 430. Upper feature point 930 and lower feature point 932 may be any salient feature points related to OF-R 135-R in the AP preoperative image 430. For example, in some embodiments, upper reference line 924 and lower reference line 926 may be tangential to the upper and lower boundaries, respectively, of OF-R 135-R in the AP preoperative image 430. Thus, in some embodiments, obturator angle 920 may be determined based on three pelvic feature points—(1) PS 130 (e.g. the inferior PS 130 as the vertex), (2) upper feature point 930 (e.g. a tangent point on a line drawn from PS 130 in (1) and tangent to the upper boundary of OF-R 135-R in AP preoperative image 430), and (3) lower feature point 932 (e.g. tangent point on a line drawn from PS 130 in (1) above and tangent to the lower boundary of OF-R 135-R in AP preoperative image 430).

In some embodiments, obturator angle 920 may be determined automatically based on the feature points in a fluoroscopic image (e.g. preoperative image 430). In some embodiments, the program may include functionality to facilitate user adjustment of obturator angle 920. GUI 900 may include guide dots 928 to facilitate navigation and/or to facilitate adjustments to obturator angle 920. In some embodiments, the obturator angle measurement 922 may be displayed and updated as adjustments are made. GUI 900 in FIG. 9 also shows circle 520 as centered in the acetabulum, aligned digital femoral template 220, pelvic reference line 720, pelvic teardrop radiographical feature 820, as well as previously identified feature points 130, GT-R 120-R, etc. Preoperative image 430 may be stored with all annotations, feature points, aligned templates, etc. and appropriately labeled for easy retrieval.

Figure 10:
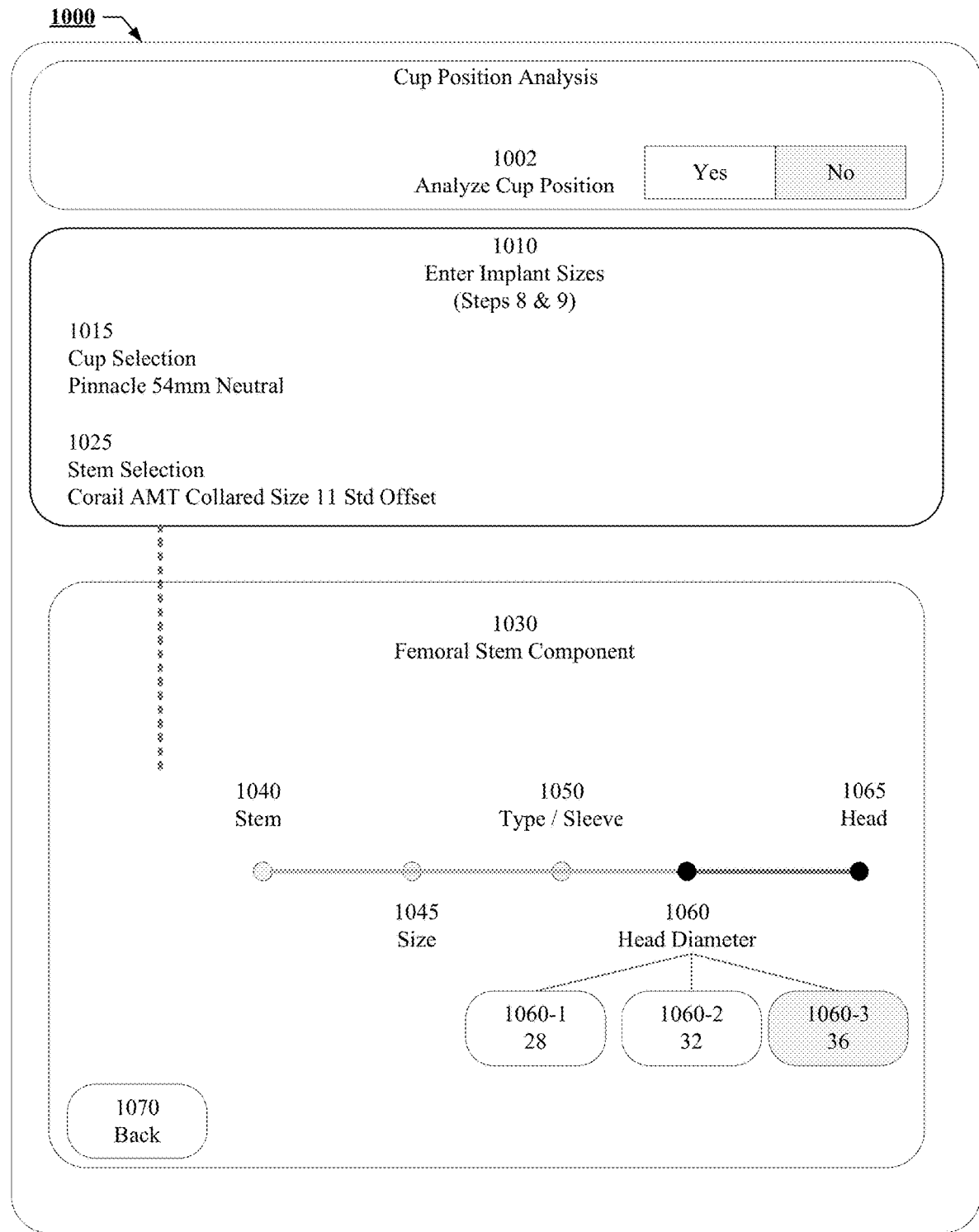
FIG. 10 shows a representation of another GUI menu presented to a user for intraoperative selection of implant sizes and implant components to facilitate intraoperative analysis and modeling.

FIG. 10 shows a representation of GUI menu 1000 presented to a user for intraoperative selection of implant sizes and implant components to facilitate intraoperative analysis and modeling. GUI 1000 may be presented to the user as part of intra-operative menu 320 (FIG. 3).

As shown in FIG. 10, cup position analysis, which is provided by functionality associated with selection 1002 "Analyze Cup Position" has been skipped (as indicated by the "NO" selection).

GUI 1000 may include a plurality of selections, where a menu selection may bring up an interface to enter size information pertaining to the selection. For example, in GUI 1010, implant sizes may be entered. As shown in FIG. 10, Cup Selection information element (IE) 1015 indicates "Pinnacle 54 mm Neutral" as the acetabular cup (e.g. corresponding to acetabular cup 230 of hip prosthesis 200 in the template image of FIG. 2) selection, and Stem Selection IE 1025 indicates "Corail AMT Collared Size 11 Std. Offset" as the stem selection (e.g. corresponding to femoral stem 240 of hip prosthesis 200 in FIG. 2). The selections above may be entered based on initial selections by a surgeon (e.g. based on preoperative analysis and/or measurements). Various other parameters pertaining to the implants may also be entered (as indicated by the dashed lines) as appropriate.

Further, as shown in FIG. 10, upon selecting "Femoral Stem Component" 1030 a user may enter other stem parameters 1040, size parameters 1045, and type/sleeve parameters 1050. The user may also select Head Diameter 1060 such as one of: head diameters 1060-1 of size 28, 1060-2 of size 32, or 1060-3 of size 36. In FIG. 10, head diameter 1060-3 of size 36 has been selected. The component, size, and parameter selections in GUI 1000 may be used to create an appropriate trial (or final) digital template and/or to perform intraoperative analysis such as determination of various biomechanical parameters.

Figure 11:
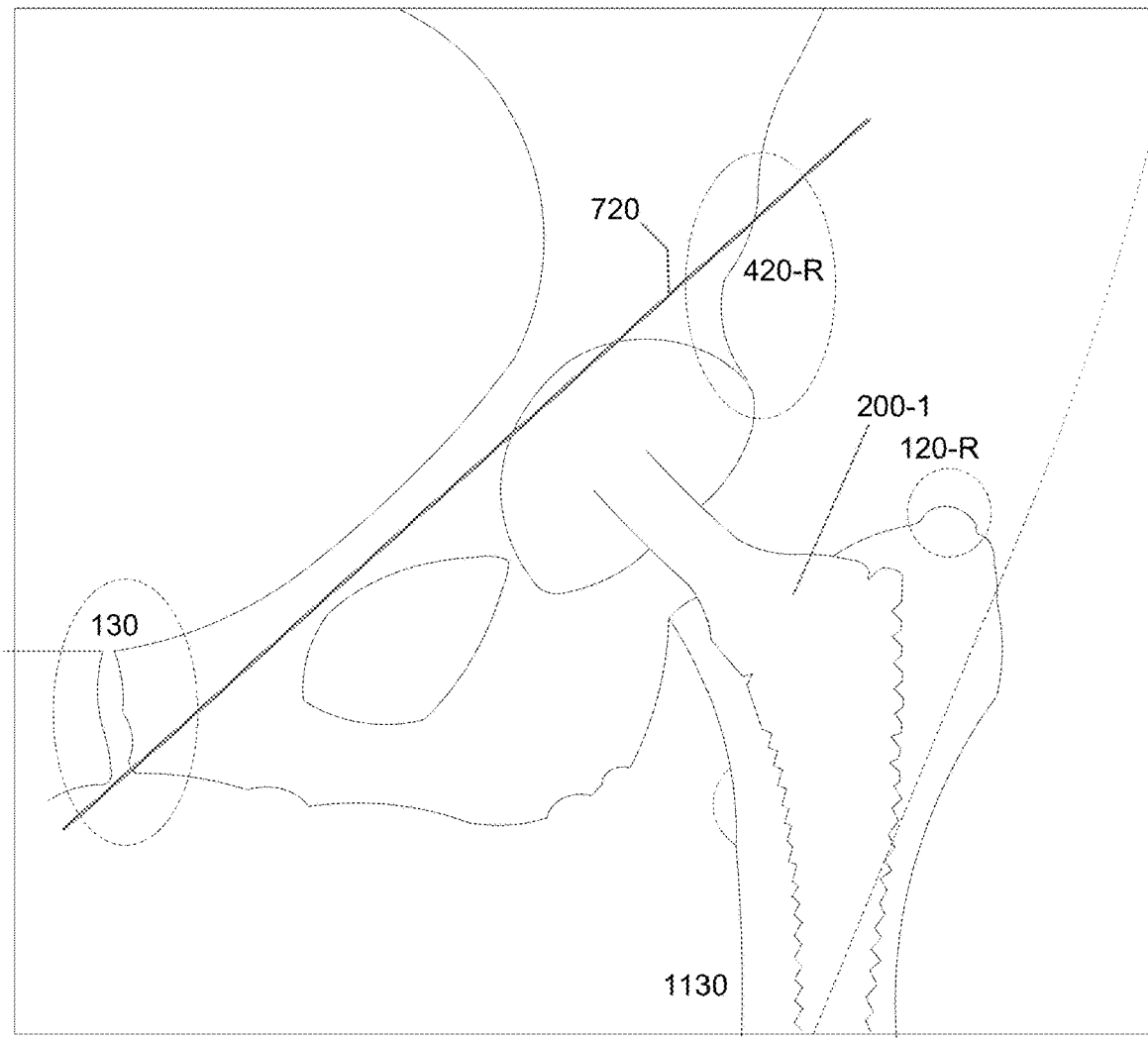
FIG. 11 shows a GUI of an intraoperative image taken after a hip reduction in accordance with certain disclosed embodiments.

FIG. 11 shows a GUI 1100 of an intraoperative image 1130 taken after a hip reduction in accordance with certain disclosed embodiments. In some embodiments, GUI 1100 may also display a trial prosthesis or a digital template image of a hip prosthesis 200-1 based on the selections, measurements, and parameters entered in GUI 1000 (FIG. 10). Accordingly, in some embodiments, in GUI 1100, the digital template image displayed may be based on selected implant and component sizes.

GUI 1100 displays the current operation shown as "Import Second Image—X-Ray of Ipsilateral Hip," which is further specified as an Anterior-Posterior "AP Hip X-ray Taken After Hip Reduced" in window 1110. As shown in FIG. 11, femoral osteotomy has been performed and the femoral head FH-R 115-R and femoral neck FN-R 150-R have been removed.

FIG. 11 shows example anatomical features such as PS 130, GT-R 120-R, and a section of the pelvic bone (PB) above the acetabulum (shown as PB-R 420-R in FIG. 11) that were also identified in the preoperative image. In some embodiments, the anatomical features may be automatically detected. In some embodiments, a user may be asked to confirm identified features, and/or locate/relocate any identified features (e.g. PS 130, GT-R 120-R, and PB 420).

As shown in FIG. 11, GUI 1100 may also include a Tips window 1140, which provides user guidance. For example, Tips window may instruct the user to "Maintain the same C-arm position used in the PreOp hip image when taking the IntraOp hip image," "Center [the] acetabulum in the image", confirm that the "Greater trochanter, femoral diaphysis, pubic symphysis, & pelvic bone above acetabulum [are] shown," in the image, and (e.g. when capturing an image of a patient's hip) to ensure that the patient's "leg [is placed] in 10 Degrees of internal rotation and [that the] C-arm [is rainbowed] 10 Degrees over the top to show patient's true offset." Tips window 1140 and example anatomical features shown in FIG. 11 are merely examples to illustrate operation and the tips shown and/or features identified in FIG. 11 may vary depending on the medical procedure.

Although the "Tips" window 1140, instruct the user to "Maintain the same C-arm position used in the PreOp hip image when taking the IntraOp hip image," in practice, the intraoperative C-arm position may differ from the preoperative C-arm position. The difference in position may cause analysis errors that, in conventional schemes, may not be detected until the end stages of the analysis, thereby, increasing the likelihood of errors, lengthening operation time, etc. Disclosed embodiments aim to detect C-arm position differences early in the process and closer to the time the actual intraoperative image is taken, so that C-arm positioning errors can be corrected and guidance provided to operators in a timely manner.

Figure 12A:
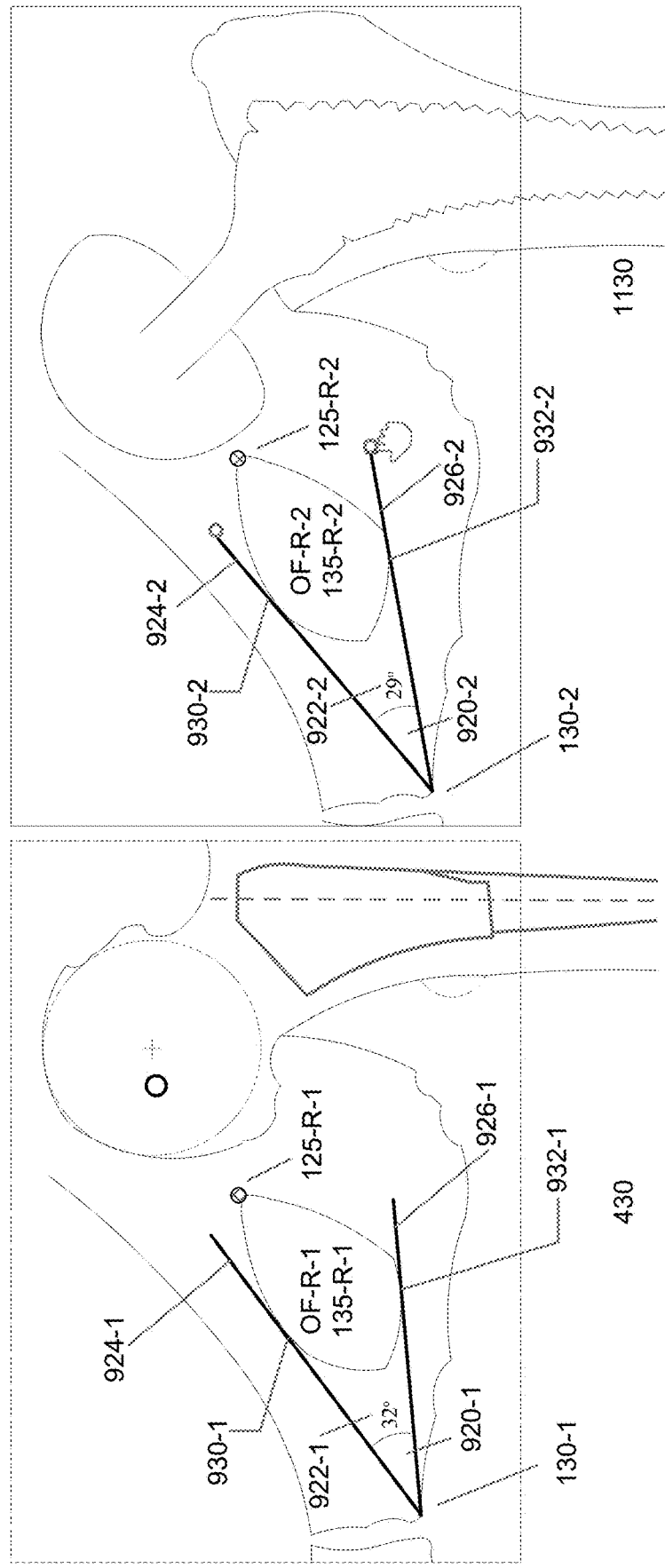
FIGS. 12A and 12B show a preoperative image indicating a first obturator angle and the marking of a second obturator angle in the intraoperative image in accordance with certain disclosed embodiments.
Figure 12B:
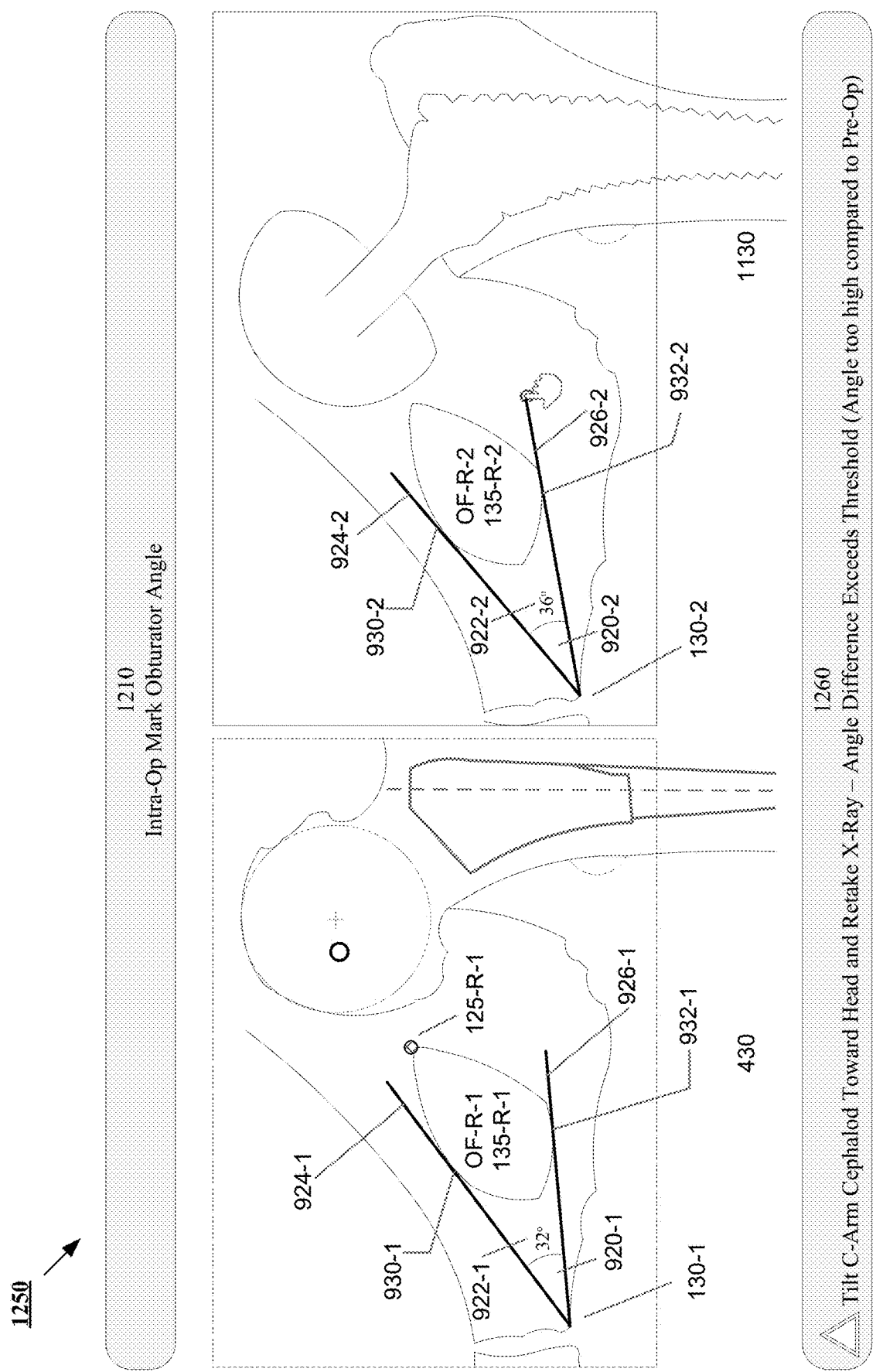

FIGS. 12A and 12B show (on the left) preoperative image 430 (as shown in FIG. 9) indicating a first obturator angle 922-1 and (on the right) the marking of a second obturator angle 922-2 in the intraoperative image 1130 (as shown in FIG. 11) in accordance with certain disclosed embodiments.

GUI 1200 provides a description of the current operation 1210 shown as "Intra-Op Mark Obturator Angle," which indicates that the intraoperative obturator angle 922-2 is being determined in the intraoperative image 1130. As seen in FIG. 12A, correspondences may be established between the first (left hand side) preoperative image 430 (shown in FIG. 9) and the second (right hand side) intraoperative image 1130 (shown in FIG. 11). In FIGS. 12A and 12B, the suffix "-1" is added to labels to identify features in the first preoperative image, while the suffix "-2" is added to labels to identify similar or corresponding features in the second intraoperative image.

For example, in FIG. 12A, features such as inferior PS 130-1 and TD 125-R-1 in the first (preoperative) image 430 correspond to features inferior PS 130-2 and TD 125-R-2, respectively, in the second (intraoperative) image 1130. Further, in some embodiments (e.g. as discussed in relation to FIG. 9), a first preoperative obturator angle 920-1 may be formed with inferior PS 130-1 as the vertex, by the intersection of first upper reference line 924-1 from pubic symphysis (PS) 130-1 to a first upper preoperative feature point 930-1 on a upper boundary of OF-R-1 135-R-1 in preoperative image 430 and first lower reference line 926-1 from the PS 130-1 to a first lower preoperative feature point 932-1 on a lower boundary of OF-R-1 135-R-1 in preoperative image 430.

In some embodiments, a second intraoperative obturator angle 920-2 may be formed with inferior PS 130-2 as the vertex, by the intersection of corresponding second upper reference line 924-2 from PS 130-2 to a corresponding second upper intraoperative feature point 930-2 on a upper boundary of OF-R-2 135-R-2 in intraoperative image 1130 and corresponding second lower reference line 926-2 from PS 130-2 to a corresponding second lower intraoperative feature point 932-2 on a lower boundary of OF-R-2 135-R-2 in intraoperative image 1130. In some embodiments, obturator angle 920-2 may be determined automatically based on feature points in fluoroscopic image 1130.

In some embodiments, the program may include functionality to facilitate user adjustment of obturator angle 920-2. For example, GUI 1200 may include guide dots (not shown in FIG. 12A) or an "angle tool" (e.g. showing automatically determined reference lines 922-2 and 924-2) to facilitate adjustments to obturator angle 920-2. In some embodiments, the obturator angle measurement 922-2 may be displayed and updated as adjustments are made. In some embodiments, the "angle tool" to make changes to the obturator angle may automatically appear when intraoperative image 1130 is loaded or selected, when preoperative image 430 includes obturator angle measurements. In some embodiments, one or more of: the angle tool, automatically determined reference lines 922-2 and 924-2, and/or automatically determined angle measurement 922-2 may appear first upon loading or receiving captured intraoperative image 1130 and determination of obturator angle 920-2 may precede other intra-operative image operations.

As shown in FIG. 12A, preoperative obturator angle measurement 922-1 is 32 degrees, while intraoperative obturator angle measurement 922-2 is 29 degrees. If the measured preoperative obturator angle (922-1) exceeds the measured intraoperative obturator angle (922-2) by more than a threshold (e.g. 2 degrees), then, in window 1240, the operator is informed that the "Angular Difference exceeds the threshold" and further that the intraoperative "angle [920-2 is] too low [when] compared to the preop[erative angle]" and is therefore instructed to "Tilt [the] C-arm Cepahalod Toward [the] Feet [of the patient] and Retake [the] X-Ray." The threshold may be set by the surgeon, or may be a predetermined threshold based on accepted standards. In some embodiments, the threshold may be set at 2 degrees.

FIG. 12B shows GUI 1250, which is the similar to GUI 1200. FIG. 12B illustrates a situation where the measured intraoperative obturator angle (922-2) exceeds the measured preoperative obturator angle (922-1) by more than a threshold (e.g. 2 degrees). As shown in FIG. 12B, preoperative obturator angle measurement 922-1 is 32 degrees, while intraoperative obturator angle measurement 922-2 is 36 degrees. If the measured preoperative obturator angle (922-1) is less than the measured intraoperative obturator angle (922-2) by more than the threshold (e.g. 2 degrees), then, in window 1260, the operator is informed that the "Angular Difference exceeds the threshold" and further that the intraoperative "angle [920-2 is] too high [when] compared to the preop[erative angle 920-1]" and is therefore instructed to "Tilt [the] C-arm Cepahalod Toward [the] Head [of the patient] and Retake [the] X-Ray." Although windows 1240 and 1260 refer to the "Feet" and "Head" of the patient, in general, any appropriate salient anatomical feature visible to the operator may be used to guide C-arm movement.

In instances, where the measured intraoperative obturator angle (922-2) and the measured preoperative obturator angle (922-1) do not differ by more than the threshold (e.g. absolute difference ≤2 degrees), then an indication may be provided (e.g. in a window) that the intraoperative image is acceptable and that further analysis (e.g. to intraoperatively assess and/or determine biomechanical parameters associated with the prosthesis and/or the patient) may proceed. Thus, medical personnel are provided with an early indication of intraoperative image suitability for further intraoperative assessment and/or analysis of biomechanical parameters. In addition, when the intraoperative image is determined not to be suitable, the operator is provided an indication of the error, an indication of whether the intraoperative angle is too low or too high, and C-arm repositioning instructions. As outlined above, the C-arm repositioning instructions (when the image is to be retaken) may be based on any appropriate salient anatomical patient features visible to the operator thereby simplifying operator guidance.

Figure 13:
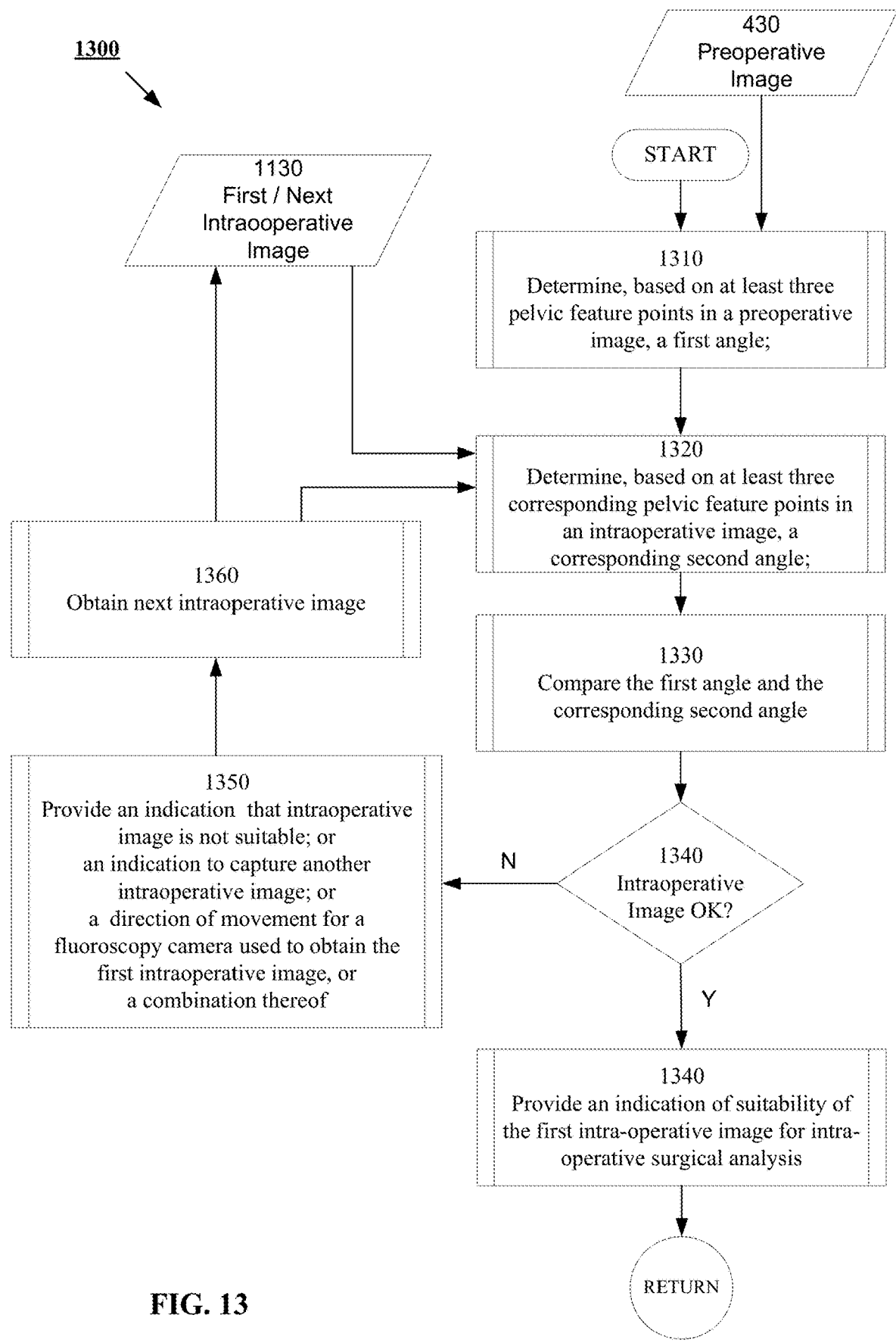
FIG. 13 shows a flowchart illustrating a method for determining the suitability of an intraoperative image for further intraoperative surgical analysis.

FIG. 13 is a flowchart illustrating a method 1300 for determining the suitability of an intraoperative image for further intraoperative surgical analysis. In some embodiments, method 1300 may be performed on a processor, computer, computing subsystem, or computing device, which may be coupled to an imaging device such as a fluoroscopic imaging device, and to a display. In some embodiments, method 1300 may be triggered on initial receipt of the first (or next) intraoperative image.

In step 1310, a first angle (e.g. obturator angle 920-1) may be determined based on at least three pelvic feature points in a pre-operative image (e.g. preoperative image 430). In some embodiments, the first angle (e.g. obturator angle 920-1) may be obtained from a previously stored preoperative image, which includes (or has been annotated with) the first angle information.

In step 1320, a corresponding second angle (e.g. obturator angle 920-2 corresponding to obturator angle 920-1) may be determined based on at least three corresponding pelvic feature points in an (first or next) intraoperative image (e.g. intraoperative image 1130).

In step 1330, the first angle (e.g. obturator angle 920-1) and the corresponding second angle (e.g. obturator angle 920-2) may be compared.

In some embodiments, a first obturator angle (e.g. obturator angle 920-1) may be used as the first angle. The first obturator angle (e.g. obturator angle 920-1) may be formed with a vertex at an inferior Pubic Symphysis (e.g. PS-1 130-1) by the intersection of a first upper reference line (e.g. 924-1) from the inferior PS (e.g. PS-1 130-1) to a first upper feature point (e.g. 930-1) on an upper boundary of an OF (e.g. OF-R-1 135-R-1) in the preoperative image and a first lower reference line (e.g. 926-1) from the inferior PS 130-1 to a first lower feature point (e.g. 932-1) on a lower boundary of the of the OF (e.g. OF-R-1 135-R-1) in the preoperative image. In some embodiments, the first upper reference line (e.g. 924-1) and first lower reference line (e.g. 926-1) may be tangential (e.g. first upper feature point 930-1 and first lower feature point 932-1 may be tangent points) to the upper and the lower boundaries of OF-R-1 135-R-1, respectively.

Further, in some embodiments, a second obturator angle (e.g. obturator angle 920-2) may be used as the corresponding second angle. The second obturator angle (e.g. obturator angle 920-2) may be formed (e.g. in the second intraoperative image 1130) with a vertex at the corresponding inferior PS (e.g. PS-2 130-2) by the intersection of a corresponding second upper reference line (e.g. 924-2) from the corresponding inferior PS (e.g. PS-2 130-2) to a corresponding second upper feature point (e.g. 930-2) on the upper boundary of a corresponding OF (e.g. OF-R-2 135-R-2) in the intraoperative image (e.g. intraoperative image 1130) and a corresponding second lower reference line (e.g. 926-1) from the corresponding inferior PS-2 130-2 to a corresponding second lower feature point (e.g. 932-2) on a lower boundary of the corresponding OF (e.g. OF-R-2 135-R-2) in the intraoperative image. In some embodiments, the corresponding second upper reference line (e.g. 924-2) and corresponding second lower reference line (e.g. 926-2) may be tangential (e.g. corresponding second upper feature point 930-2 and corresponding second lower feature point 932-2 may be tangent points) to the upper and the lower boundaries of the corresponding OF-R-2 135-R-2, respectively.

In step 1340, based on the comparison in step 1330 ("Y" in step 1330), an indication of suitability of the (first or next) intra-operative image 1130 for intra-operative surgical analysis may be provided. For example, when the absolute value of the difference between obturator angle 920-1 and corresponding obturator angle 920-2 does not exceed a threshold, then, an indication may be provided that intraoperative image 1130 is suitable for further intraoperative analysis.

Method 1300 may be performed intraoperatively during a hip arthroplasty procedure and, in response to a determination of suitability of the first intraoperative image, further intraoperative surgical analysis may include a determination of at least one of: leg length offset, or acetabular anteversion, or acetabular inclination, or acetabular retroversion, or parameters indicative of centers of rotation, or some combination of the above. The method may then return control to a calling program or routine.

In step 1350, based on the comparison in step 1330 ("N" in step 1330), an indication that the (first or next) intraoperative image 1130 is not suitable for intra-operative surgical analysis may be provided. For example, when the absolute value of the difference between obturator angle 920-1 and corresponding obturator angle 920-2 exceeds a threshold, then: (a) an indication may be provided that intraoperative image is not suitable for further intraoperative analysis, and/or (b) the operator may further be instructed to capture another image, and/or (c) provided with an indication of movement direction for a fluoroscopy camera that was used to obtain the current intraoperative image 1130; or (d) some combination of (a), (b), or (c) above. In some embodiments, the indication of movement direction (when provided) may include directional instructions for movement of the fluoroscopy camera relative to salient anatomical features of a surgical subject. For example, the indication of movement direction may direct that the fluoroscopy camera be titled toward the head of the patient, or titled toward the feet of the patient based on the comparison (in step 1330). The method may then proceed to step 1360.

In step 1360, upon obtaining the next intraoperative captured image, step 1320 may be invoked to begin another iteration. In some embodiments, in response to the indication of non-suitability of the first intraoperative image, an indication of capture of a second (next) intraoperative image may be received in step 1360 (e.g. by a computer performing method 1300 from a fluoroscopic imaging system).

Method 1300 may iterate until it is determined that a suitable intraoperative image 1130 has been captured.

In instances where the fluoroscopy imaging system includes or is coupled to a robotic or automatic moving apparatus that is capable of moving the imaging device(s), angular information comprising one or more of: (a) the first obturator angle and the second obturator angle and/or (b) the difference between the first obturator angle and the second obturator angle may be provided to the fluoroscopy imaging system and/or to the robotic or automatic moving apparatus. The fluoroscopy imaging system and/or the robotic or automatic moving apparatus may use the angular information (e.g. along with any previously stored calibration parameters) to make appropriate camera pose adjustments, capture another image when triggered, and indicate availability of the second image.

In hip arthroplasty, for example, further intraoperative analysis may calculate intraoperative changes in offset and leg length, for a selected hip prosthesis 200 (or a component part of hip prosthesis 200) using at least one center of rotation associated with the prosthesis, as well as features in preoperative image 430, and intraoperative image 1130. Thus, for intraoperative analysis, preoperative image 430 and/or intraoperative image 1130 may be consistently scaled. Further, at least one stationary point on a stationary anatomic region (such as the pelvis) in both images is identified in each image. In addition, a center of rotation of the prosthetic in the intraoperative image 1130 may be determined. One center of rotation in intraoperative image 1130 may be determined by overlaying an acetabular template, or other digital annotation on intraoperative image 1130.

As another example of intraoperative analysis, a femoral implant may be modeled using a digital template or other digital annotation and by using at least one landmark point on a non-stationary anatomic region (such as on femur F 150) in both the preoperative image 430 and intraoperative image 1130 to generate data about how changing the modeled implant, that is, replacing or modifying the implant in at least one dimension, can affect offset and leg length. This additional intraoperative analysis enables a surgeon to understand how changing an implant intraoperatively would affect offset and leg length prior to making actual changes.

Accordingly, (i) at least one of a preoperative ipsilateral (or an inverted contralateral) image 430 (referred to herein as preoperative image 430) may be obtained along with (ii) a suitable intraoperative image (e.g. determined as suitable using the procedure in FIG. 13). The preoperative image 430 and intraoperative image 1130 may be scaled and aligned using a variety of techniques. In some embodiments, the preoperative image 430 and intraoperative image 1130 may be displayed, side by side or overlaid to facilitate further analysis.

As one example, the system may generate at least one stationary point (e.g. TD 125) on the stationary anatomic region in both preoperative image 430 and intraoperative image 1130. Further, the system may generate a digital representation such as a digital template or other digital annotation, such as a digital line having at least two points, e.g. a line representing a longitudinal axis or a diameter of an implant or a bone, or a digital circle, which indicates the actual prosthetic component (e.g. acetabular component 230) placement and a corresponding center of rotation for that component (e.g. acetabular component 230).

In some instances, an additional digital template or other representative digital annotation related to another prosthetic (e.g. femoral stem 240) may be used indicate placement in intraoperative image 1130. In the example above, the femoral stem (240) and acetabular component (230) templates, or representative annotations, generated on the intraoperative image 1130 are connected at the center of rotation (e.g. as described in relation to FIG. 2) and may replicate the actual positioning of the (to be implanted) prosthetic femoral stem and acetabular components. The system may further generate at least one landmark point on the femoral anatomy, consistently identified in both images (such as a point on GT 120). In some embodiments, the system may use this landmark point (e.g. GT 120) to calculate estimated changes to offset and leg length for possible replacement prosthetics if a surgeon were to change femoral stem implant selection.

The landmark point may also be used to position (i) a femoral component image, (ii) intraoperative overlay image 1130 or a portion thereof, or a portion of the intraoperative prosthesis and a portion of the bone of the patient in which the prosthesis is implanted, as described below in relation to FIGS. 14-23, (iii) a femoral template (e.g. a digital template of at least the intraoperative femoral stem and/or a digital template of the acetabular cup) or (iv) surrogate digital annotation in the preoperative image.

In some embodiments, the system may determine a vector in intraoperative image 1130 using the stationary pelvic TD 125 as the origin, with the vector being directed to and terminating at the acetabular cup location, as determined by the center of rotation of an acetabular component, or representative acetabular template. The term vector is utilized herein to mean Euclidean vector having an initial point or "origin" and a terminal point, with a magnitude (e.g. vector length) and direction (between the origin and the terminal point). In some embodiments, the system may position an acetabular component template or representative digital annotation, such as a digital line or digital circle, in preoperative image 430 based on the above vector.

In some embodiments, a femoral stem template or representative digital annotation may be generated in preoperative image 430 using information from the generated annotations and templates in intraoperative image 1130 but without generating a femoral component template or representative annotation in intraoperative image 1130. For example, the system may determine a vector between the generated landmark point on the femoral anatomy (preferably the greater trochanter) and the center of rotation of the acetabular component template. The system may also analyze positional differences between femur F 155 in preoperative image 430 and femur F 155 in intraoperative image 1130, relative to the stationary pelvis, and rotate the vector to account for any differences. Examples of above techniques are illustrated and described below in relation to FIGS. 14-23.

Figure 14:
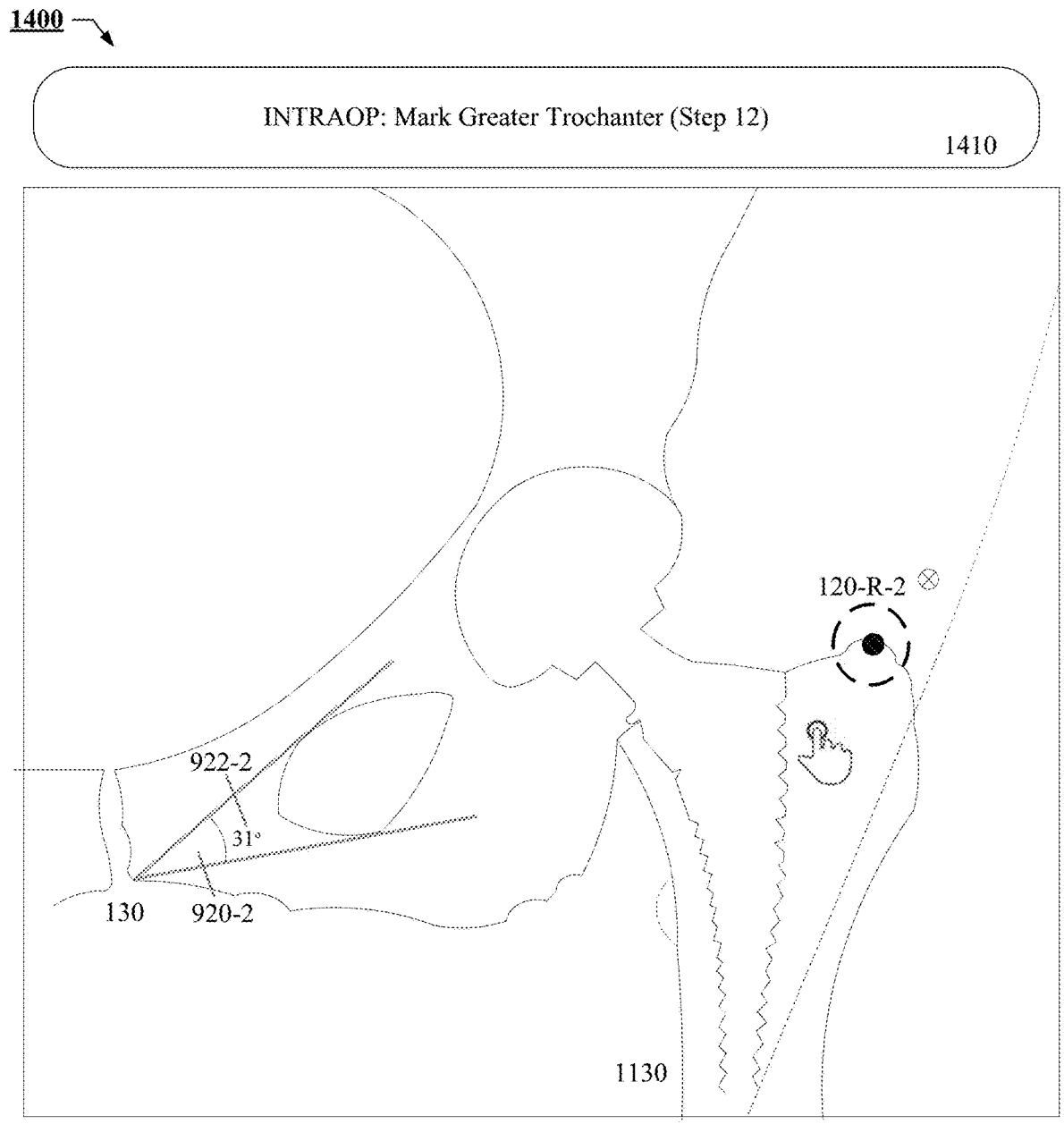
FIG. 14 is an example GUI displaying an intraoperative fluoroscopic image of a portion of the pelvic girdle of a patient.

FIG. 14 is an example GUI 1400 displaying intraoperative fluoroscopic image 1130 of a portion of the pelvic girdle of a patient. In some embodiments, intraoperative fluoroscopic image 1130 may be automatically obtained and/or displayed when an image is received by the system. In other embodiments, the intraoperative image may be stored and retrieved (e.g. using functionality provided by Add X-Ray 318 and/or another module in Intraoperative Menu 320 GUI 300 in FIG. 3).

In some embodiments, window 1410 may provide a description of the image being shown and/or current operation, which may include appropriate annotations by medical personnel. For example, GUI 1410 describes the operation on intraoperative image being shown in 1130 as an "INTRAOP: Mark Greater Trochanter". FIG. 14 shows example anatomical features such as PS 130, and GT-R-2 120-R-2, which may have been automatically identified.

FIG. 14 also shows the angle tool with the intraoperative obturator angle 920-2 and angular measurement 922-2. In some embodiments, a user may be asked to confirm identified features, and/or locate/relocate the identified features (e.g. PS 130, GT-R-2 120-R-2). As shown in FIG. 14, GUI 1400 may include guide dots and/or other tools to facilitate user positioning/repositioning of identified features. In FIGS. 14-22, the feature points shown and information displayed (e.g. tools, tips, guides, etc.) may be based on one or more of program settings, a user profile, and/or a patient profile.

Figure 15:
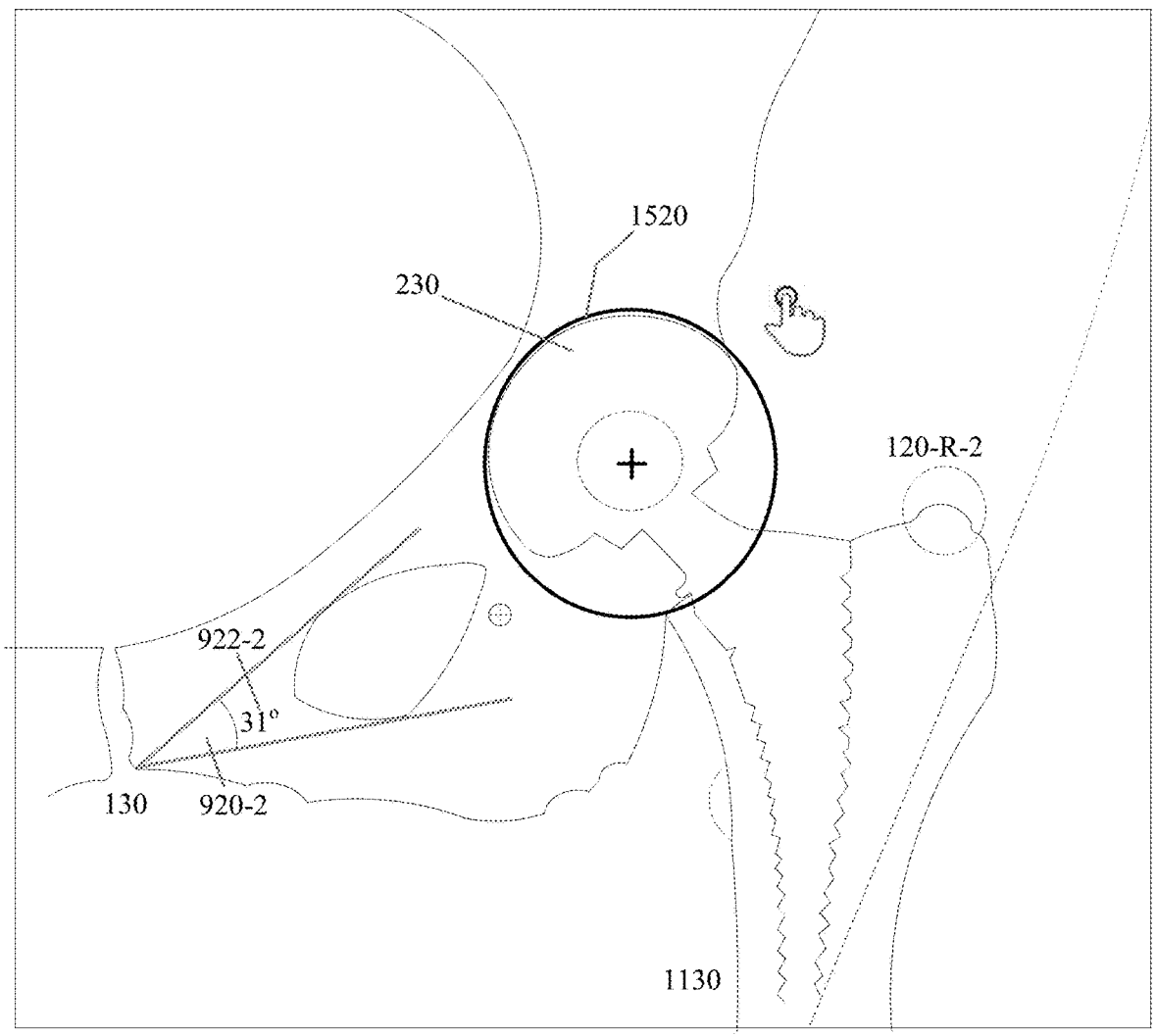
FIG. 15 shows an example GUI displaying an intraoperative fluoroscopic image illustrating a circle drawn around an acetabular component in accordance with certain disclosed embodiments.

FIG. 15 shows an example GUI 1500 displaying intraoperative fluoroscopic image 1130 illustrating a circle 1520 drawn around the acetabular component 230 in accordance with certain disclosed embodiments. Acetabular component 230 may be a trial component, for example, in accordance with user selections (e.g. as selected/entered in FIG. 10) and/or as entered by the user (e.g. using options in GUI 1500). GUI 1500 displays the current operation in window 1510 shown as "INTRAOP: Enter Component Size and Place Circle Around Acetabulum."

In some embodiments, circle 1520 may be placed automatically based on feature points in fluoroscopic image 1130. Circle 1520 is merely an example. In general, image recognition and/or feature recognition techniques may be used to identify and locate acetabular component 230 and provide an appropriate visual, graphical, and/or other indication to the user. In some embodiments, the program may include functionality to facilitate user adjustment of the size and position of circle 1520. GUI 1500 may include guide dots to facilitate navigation, resizing, and/or repositioning of circle 1520. Circle 520 may be used (e.g. in a suitable digitally calibrated radiographic image at an appropriate stage) for analysis and/or to estimate biomechanical and other parameters. In some embodiments, GUI 1500 may also show one or more feature points such as PS 130, GT-R-2 120-R-2, intraoperative obturator angle 920-2 and intraoperative angular measurement 922-2, etc.

Figure 16:
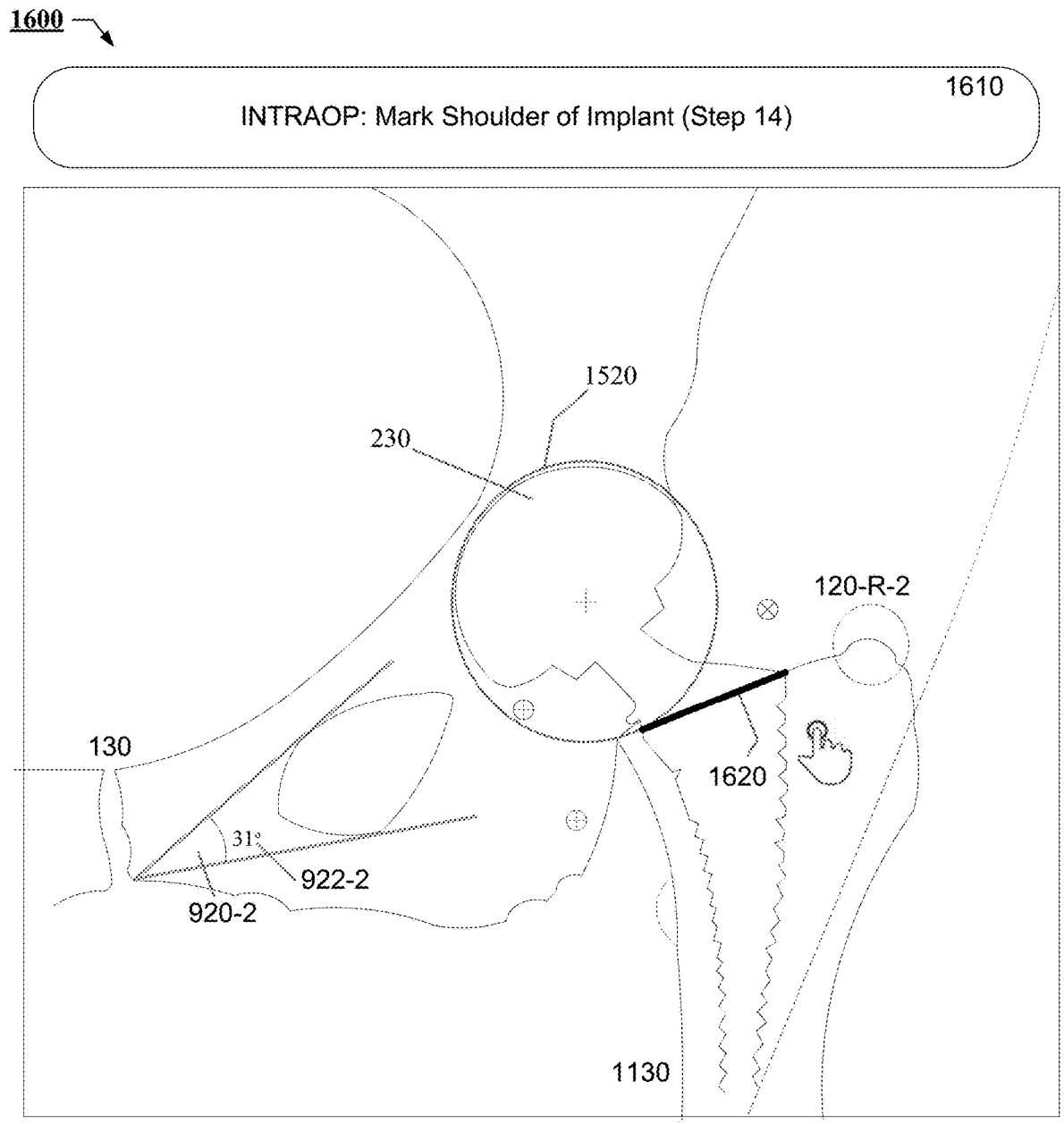
FIG. 16 shows an example GUI displaying an intraoperative fluoroscopic image illustrating the marking of a shoulder of a hip prosthesis implant in accordance with certain disclosed embodiments.

FIG. 16 shows an example GUI 1600 displaying intraoperative fluoroscopic image 1130 illustrating the marking of a shoulder of a hip prosthesis implant 1620 in accordance with certain disclosed embodiments. Hip prosthesis (e.g. hip prosthesis 200 may be a trial component in accordance with user selections (e.g. as selected/entered in FIG. 10) and/or as entered by the user (e.g. using options in GUI 1600). GUI 1600 displays the current operation in window 1610 shown as "INTRAOP: Mark Shoulder of Implant."

In some embodiments, hip prosthesis shoulder 1620 may be marked automatically based on feature points in fluoroscopic image 1130. In some embodiments, the program may include functionality to facilitate user adjustment of the size and position of the marking of hip prosthesis shoulder 1620. GUI 1600 may include guide dots to facilitate navigation, resizing, and/or repositioning when marking of hip prosthesis shoulder 1620. In some embodiments, GUI 1600 may also show one or more feature points such as PS 130, GT-R-2 120-R-2, intraoperative obturator angle 920-2 and intraoperative angular measurement 922-2, acetabular component 230 of hip prosthesis 200, circle 1520 drawn around acetabular component 1520, etc.

Figure 17:
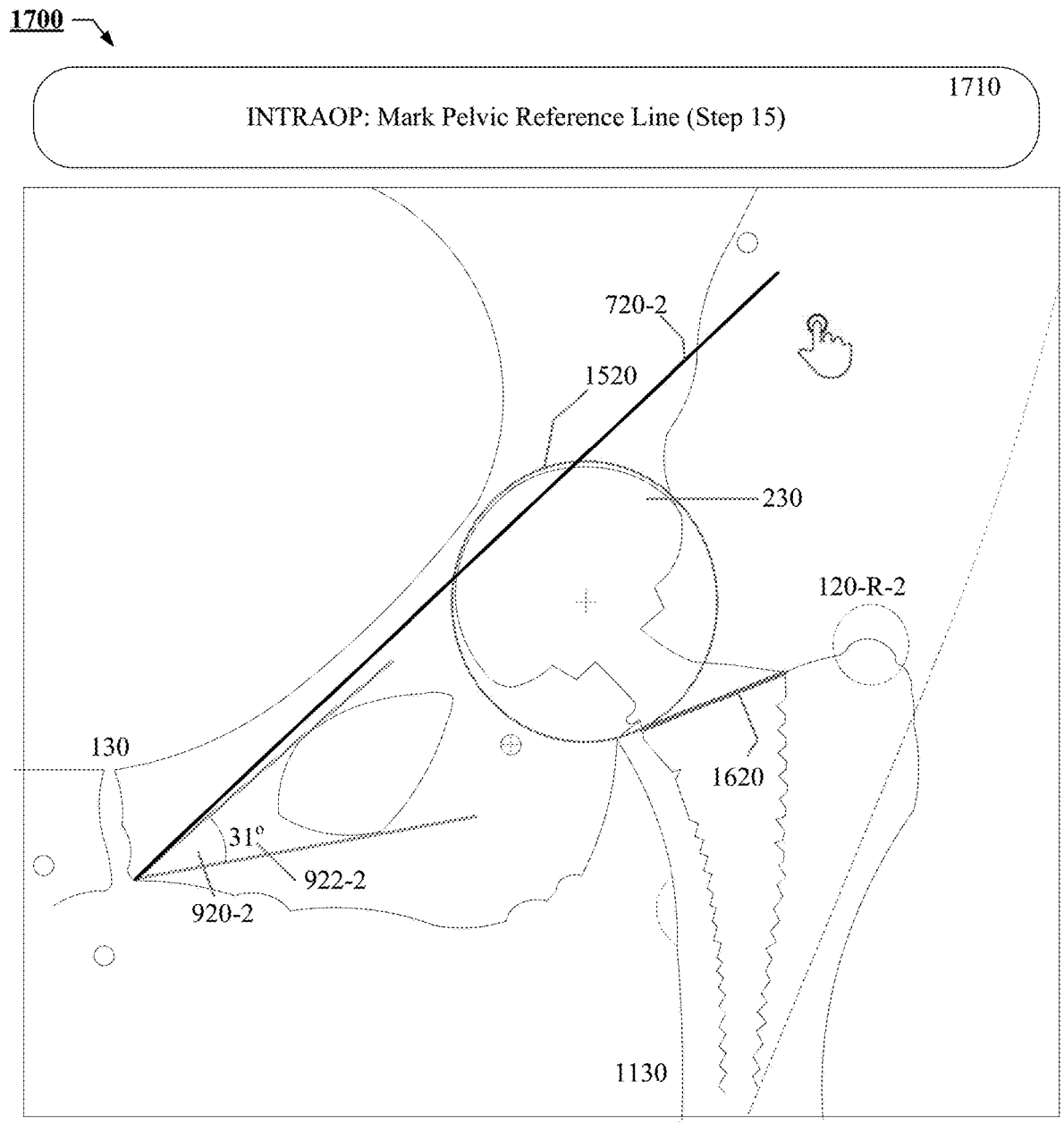
FIG. 17 shows an example GUI displaying intraoperative fluoroscopic image with pelvic reference line drawn between anatomical features in accordance with certain disclosed embodiments.

FIG. 17 shows an example GUI 1700 displaying intraoperative fluoroscopic image 1130 with pelvic reference line 720-2 drawn between anatomical features in accordance with certain disclosed embodiments. GUI 1700 displays the current operation shown as "INTRAOP: Mark Pelvic Reference Line" in window 1710. In some embodiments, pelvic reference line 720-2 may be placed automatically based on feature points in intraoperative fluoroscopic image 1130. In some embodiments, the program may include functionality to facilitate user adjustment of the position of pelvic reference line 720-2. GUI 1700 may include guide dots to facilitate navigation, sizing, and/or repositioning of pelvic reference line 720-2 in intraoperative image 1130. Pelvic reference line 720-2 may correspond, for example, to one pelvic reference lines 160, 165, or 170 (e.g. shown in FIG. 1B). For example, pelvic reference line 720-2 may correspond to reference line 170 (FIG. 1B) and begin at the inferior pubic symphysis PS 130 and extend to the right anterior superior iliac spine ASIS-R 105-R (not shown in FIG. 17). In some embodiments, pelvic reference line 720-2 may serve as a base line to facilitate image comparison and/or image registration. GUI 1700 also shows one or more feature points such as PS 130, GT-R-2 120-R-2, intraoperative obturator angle 920-2 and intraoperative angular measurement 922-2, acetabular component 230 of hip prosthesis 200, circle 1520 drawn around acetabular component 1520, marked hip prosthesis shoulder 1620, etc.

Figure 18A:
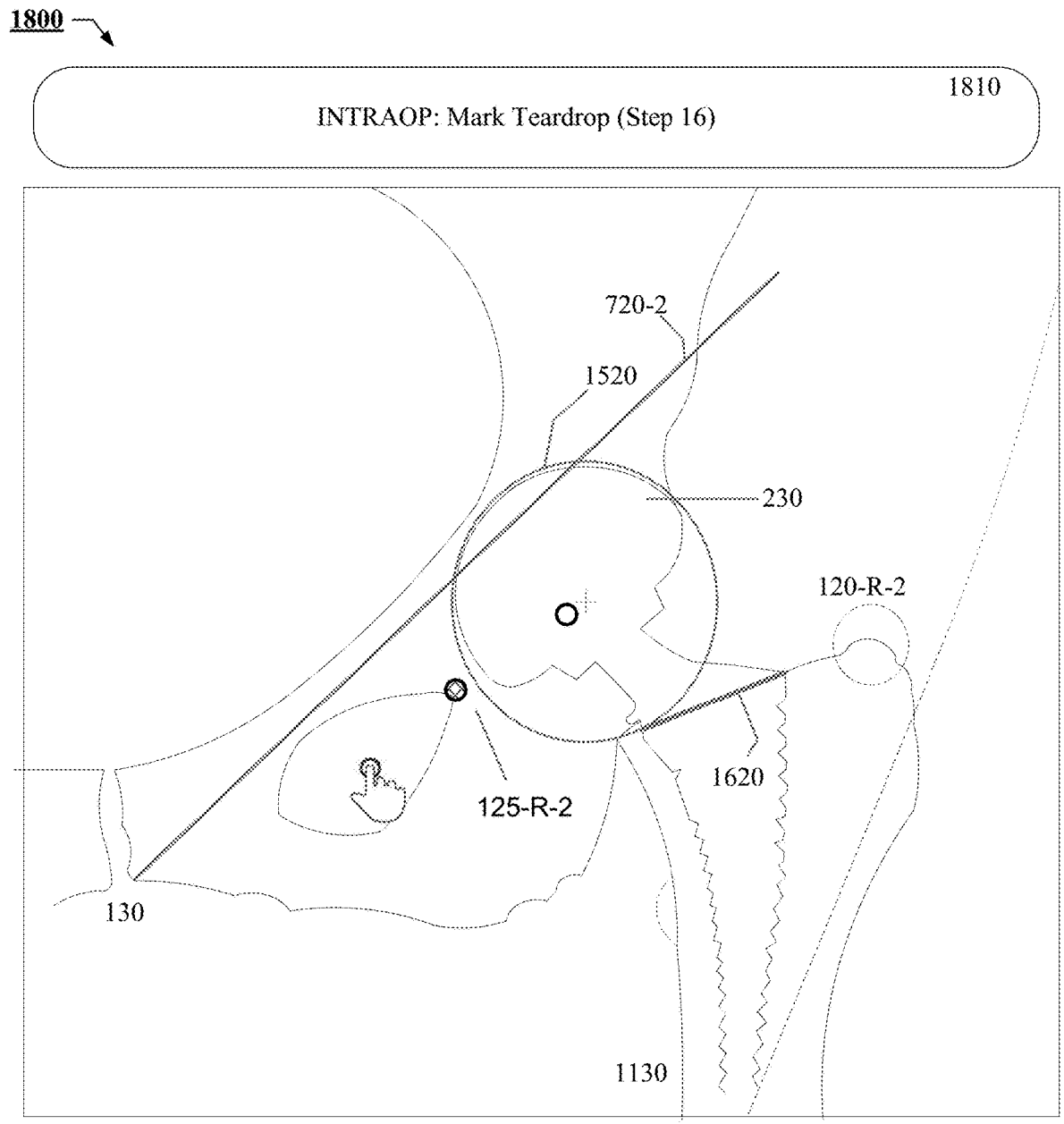
FIG. 18A shows a view of an example GUI displaying an intraoperative fluoroscopic image depicting the marking of the pelvic teardrop radiographical feature.

FIG. 18A shows a view of example GUI 1800 displaying intraoperative fluoroscopic image 1130 depicting the marking of the pelvic teardrop radiographical feature TD 125. FIG. 8 shows the intraoperative right pelvic teardrop radiographical feature TD-R-2 125-R-2. GUI 1800 displays the current operation shown as "INTRAOP: Mark Teardrop" in window 1810. In some embodiments, TD-R-2 125-R-2 may be determined automatically based on feature points in intraoperative fluoroscopic image 1130. In some embodiments, the program may include functionality to facilitate user adjustment of the position of TD-R-2 125-R-2. GUI 1800 may include guide dots to facilitate navigation and/or repositioning of TD-R-2 125-R-2 as shown in FIG. 18A. GUI 1700 also shows one or more feature points such as PS 130, GT-R-2 120-R-2, acetabular component 230 of hip prosthesis 200, circle 1520 drawn around acetabular component 1520, marked hip prosthesis shoulder 1620, pelvic reference line 720-2, etc.

Figure 18B:
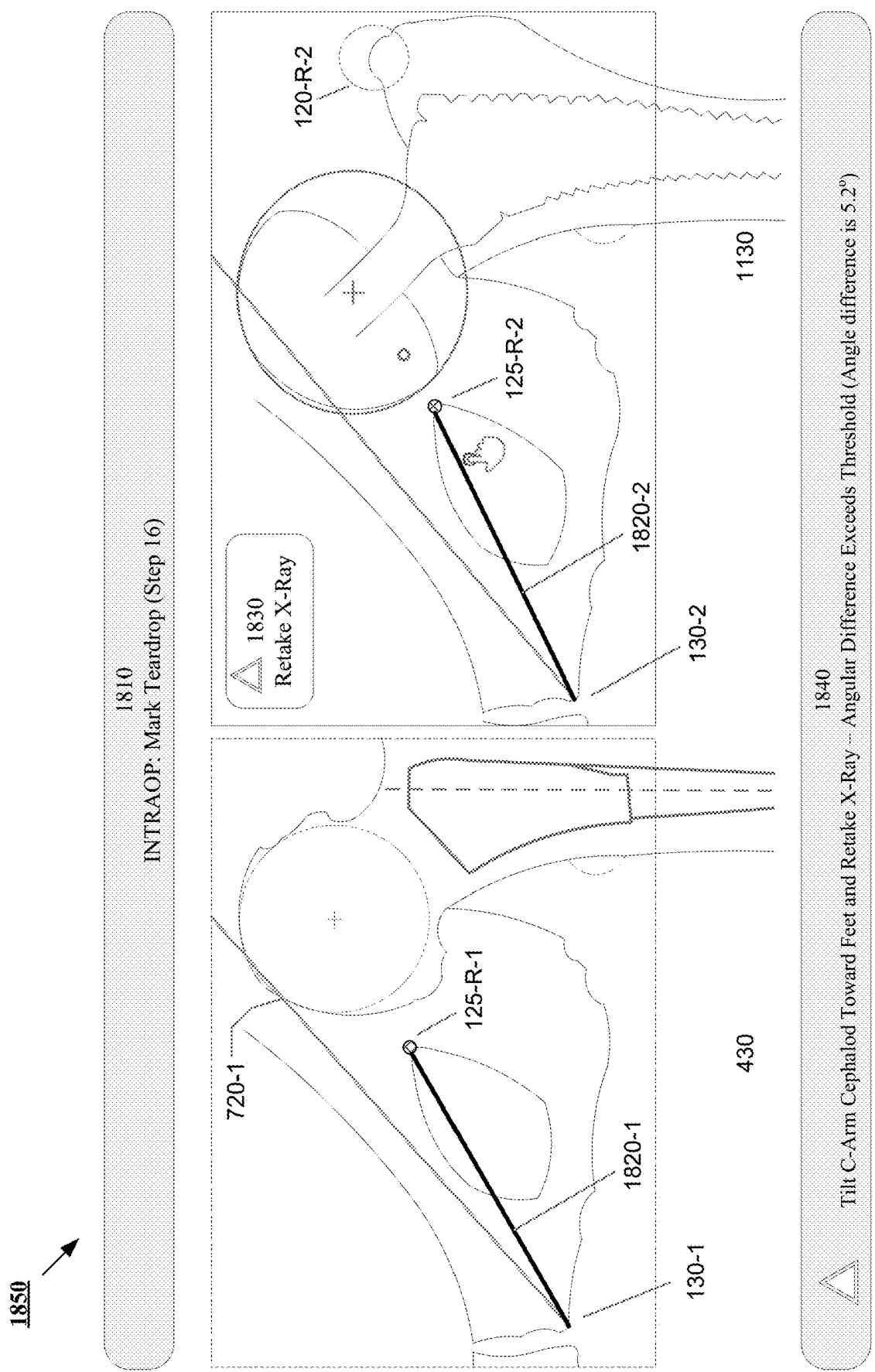
FIG. 18B shows another view of an example GUI displaying a preoperative image showing the pelvic teardrop radiographical feature alongside an intraoperative fluoroscopic image depicting the marking of the pelvic teardrop radiographical feature.

FIG. 18B shows another view of example GUI 1800 displaying intraoperative fluoroscopic image 1130 depicting (on the left) preoperative image 430 showing pelvic teardrop radiographical feature TD 125-R-1, and (on the right) the marking of the pelvic teardrop radiographical feature TD 125-R-2. FIG. 18B also shows line 1820-1 drawn between PS 130-1 and TD-R-1 125-R-1, and reference line 1820-2 drawn between PS-130-2 and TD-R-2 125-R-2.

In some embodiments, a preoperative teardrop angle may be determined based on the angle between reference line 1820-1 and another reference line such as pelvic reference line 720-1 in preoperative image 430. A corresponding intraoperative teardrop angle may be determined in intraoperative image 1130 based on the angle between reference line 1820-2 and another reference line such as pelvic reference line 720-2. When the absolute value of the difference between the preoperative TD angle and the corresponding intraoperative TD angle exceeds a threshold, a warning may be displayed, as shown in window 1830, instructing the user to "Retake the X-Ray." The warning indicates that C-arm position (e.g. relative to an anatomical feature of interest such as TD 125) at the time of capture of intraoperative image 1130 does not correspond to the C-arm position at the time of capture of the preoperative image.

In conventional systems, a determination that the relative pose of the imaging apparatus (e.g. C-arm) in the preoperative image is different from the corresponding relative pose in the intra-operative image may occur at a late stage in the analysis. Thus, a new intraoperative image is captured and may of the prior steps repeated with no guarantee that the newly captured intraoperative image will be acceptable.

In embodiments disclosed herein, an early indication of acceptability of the intraoperative image is provided (e.g. as described in relation to FIGS. 12A, 12B, and 13), thereby decreasing the likelihood that the intraoperative image will be deemed unsuitable for further intraoperative analysis at a later stage (as in FIG. 18B). Moreover, in some embodiments, even in instances where the image is deemed unsuitable for further intraoperative analysis (e.g. because of inaccuracies in the relative position of the imaging apparatus at the time of current intraoperative image capture), disclosed embodiments may provide explicit guidance on imaging apparatus positioning when capturing another intraoperative image. In some embodiments, the guidance may be based on whether the preoperative TD angle exceeds the corresponding intraoperative TD angle or vice versa (e.g. whether the corresponding intraoperative TD angle exceeds the preoperative angle). Thus, based on the angular difference and the magnitudes of the preoperative TD angle and the corresponding intraoperative TD angle, in some embodiments, the user may be instructed via window 1840 to "Tilt C-Arm Cephalod Toward Feet and Retake X-Ray—Angular Difference Exceeds Threshold (Angle difference is 5.2°)." Thus, when the intraoperative image is determined not to be suitable, the operator is provided an indication of the error, an indication of whether the intraoperative TD angle is too low or too high, and C-arm repositioning instructions. As outlined herein, the C-arm repositioning instructions (when the image is to be retaken) may be based on any appropriate salient anatomical patient features visible to the operator and providing clear guidance on the positioning/repositioning of the imaging apparatus.

Figure 19:
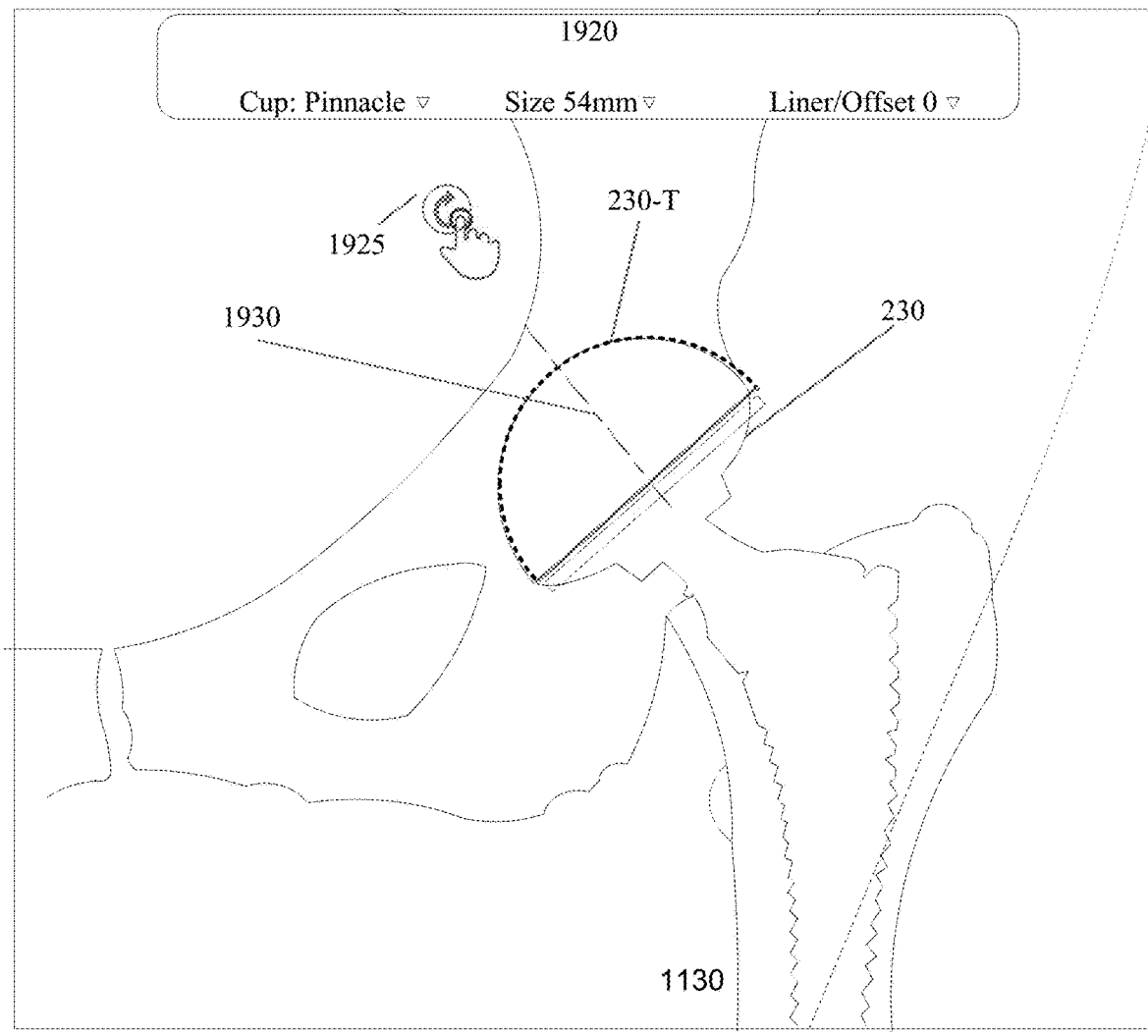
FIG. 19 shows an example GUI illustrating the alignment of a digital acetabular component template with an acetabular cup.

FIG. 19 shows an example GUI 1900 illustrating the alignment of digital acetabular component template 230-T (which may form part of digital template image of hip prosthesis 200) with acetabular cup 230 (which may be a trial prosthetic). The digital template is indicated with the suffix "-T" and is shown in FIG. 19 with dashed lines. GUI 1900 displays the current operation shown as "INTRAOP: Rotate Template to Match Cup" in window 1910. In some embodiments, window 1920 may display size, type and other parameters used to obtain the digital acetabular component template 230-T. FIG. 19 shows (in window 1920) the acetabular cup used to create digital acetabular component template 230-T as type "Pinnacle" of size "54 mm" with a Liner/Offset of 0. In some embodiments, the selected/entered sizes of the acetabular component may be used to scale the intraoperative image 1130 for overlay, matching, or comparison with preoperative image 430.

As shown in FIG. 19, digital acetabular component template 230-T may be superimposed over acetabular component 230 in intraoperative image 1130 and rotated, repositioned, and/or aligned to match with underlying acetabular component 230. For example, alignment tool 1925 may be used to rotate acetabular component template axis 1930 until digital acetabular component template 230-T is aligned with acetabular component 230 in intraoperative image 1130. In some embodiments, the digital acetabular component template 230-T may be automatically placed based on features in intraoperative image and a user may make adjustments to the position and alignment of the digital acetabular component template 230-T.

Figure 20:
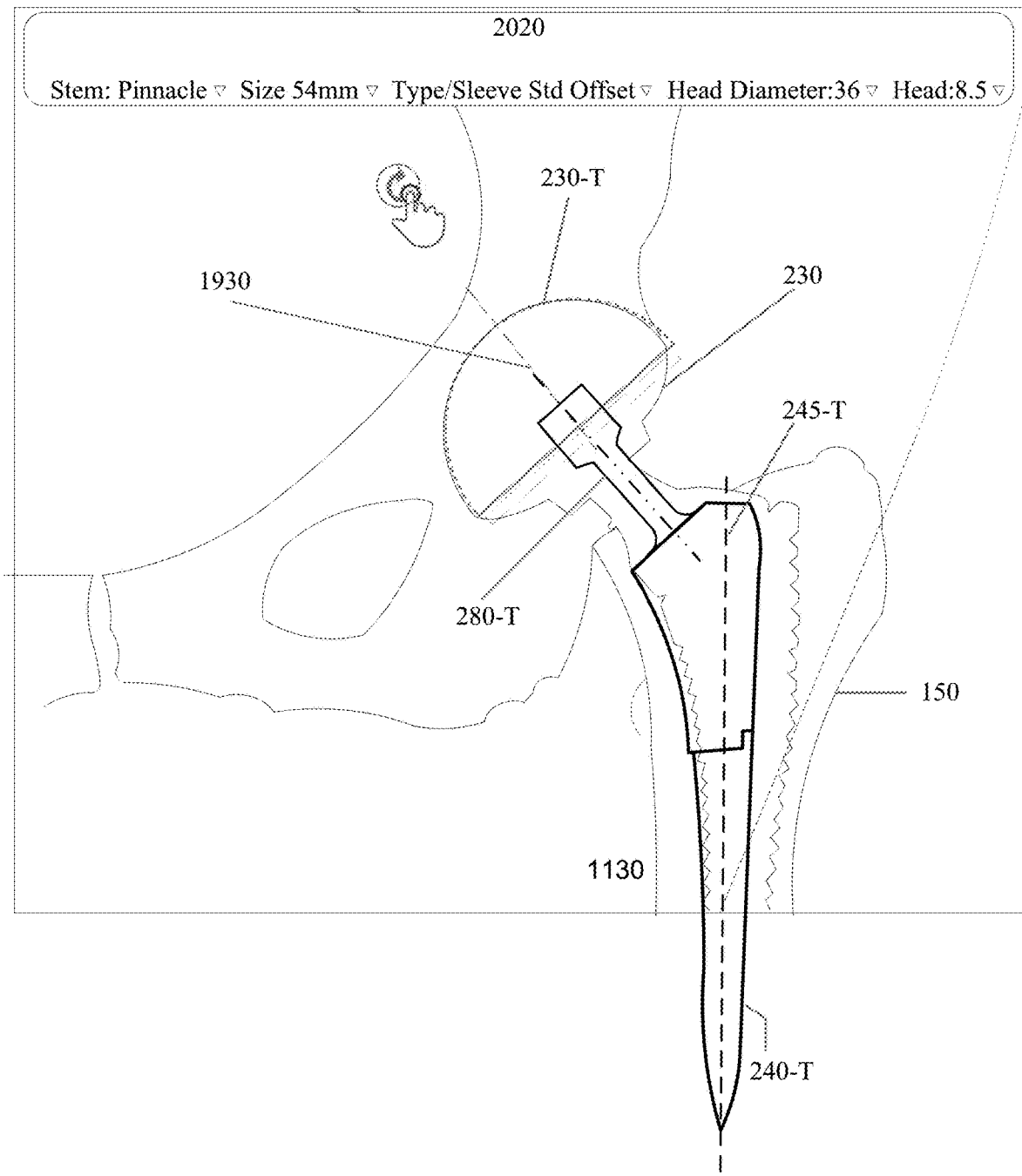
FIG. 20 shows an example GUI illustrating the alignment of a digital femoral component template with an acetabular cup.

FIG. 20 shows an example GUI 1900 illustrating the alignment of digital femoral component template 240-T (which may form part of digital template image of hip prosthesis 200) with acetabular cup 230 (which may be a trial prosthetic). The digital template is indicated with the suffix "-T". GUI 2000 displays the current operation shown as "INTRAOP: Align Femoral Template in Canal," in window 1910. In some embodiments, window 2020 may display size, type and other parameters related to the digital femoral template 220-T. For example, FIG. 20 shows (in window 2020) information pertaining to the femoral stem 240 (related to the digital femoral template 240-T) as type "Pinnacle" of size "54 mm" with Type/Sleeve as Std. Offset, Head Diameter 36, and Head 8.5.

As shown in FIG. 20, digital femoral template 240-T may be superimposed over femur F 155 in intraoperative image 1130 and rotated, repositioned, and/or aligned to match with underlying femur F 155. For example, a femoral alignment tool may be used to rotate femoral axis 245-T of digital femoral template 240-T until digital femoral template 240-T is aligned with femur F 155 in intraoperative image 1130. In some embodiments, the digital femoral template 240-T may be automatically placed based on features in intraoperative image and a user may make adjustments to the position and alignment of the digital femoral template 240-T.

Figure 21:
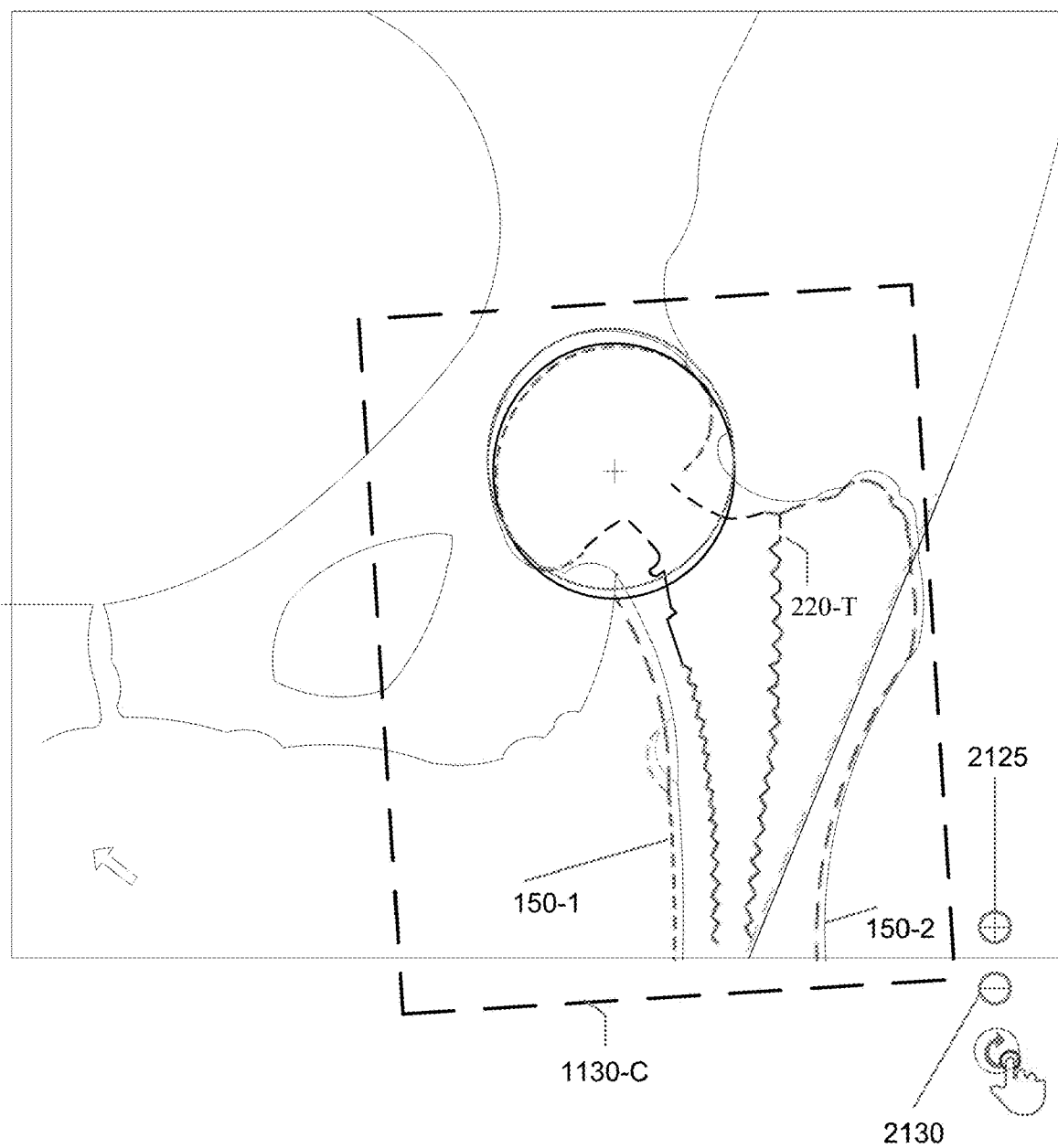
FIG. 21 shows a section or cutout of intraoperative image being overlaid on preoperative image to align femurs in the two images.

FIG. 21 shows a section or cutout 1130-C of intraoperative image 1130 (shown with dashed black lines) being overlaid on preoperative image 430 (shown with solid grey lines) to align femurs in the two images. GUI 2100 displays the current operation shown as "INTRAOP: Align Femurs," in window 2110. The suffix "-1" is used to refer to features in the preoperative image, while the suffix "-2" is used to refer to corresponding features intraoperative image 1130 or intraoperative cutout 1130-C.

Once intraoperative image 1130-C has been overlaid, the system may generate femoral template 220-T positioned on the overlaid intraoperative image 1130 so that its position in intraoperative cutout 1130-C is consistent with how femoral template 220-T was positioned in the intraoperative image (e.g. as in FIG. 20). In some embodiments, the system may remove intraoperative cutout 1130-C, while retaining the (generated) femoral template 220 overlaid on the preoperative image 430.

In some embodiments, '+' button 2125 and '−' button 2130 that facilitate manipulation of the size of intraoperative cutout 1130-C, so that the femur F 150-2 in intraoperative cutout 1130-C can precisely match femur F 150-1 in preoperative image 430. Because intraoperative image 1130 and preoperative image 430 may have already been scaled consistently (e.g. based on features, component sizes, anatomical measurements, etc.), utilization of scaling functionality may be rare and/or for fine tuning when there are small alignment and scaling differences between femur F 150-1 in preoperative image 430 and femur F 150-2 in intraoperative cutout 1130-C relative to the pelvis. Alignment differences may occur between preoperative image 430 and intraoperative cutout 1130-C because the system may have aligned the images according to the pelvis (e.g. based on pelvic reference lines 720-1 and 720-2) but the femoral axes in the images may be different. Addressing any femoral scale and alignment differences may ensure that offset and leg length parameters are calculated correctly during intraoperative analysis in subsequent steps.

Figure 22:
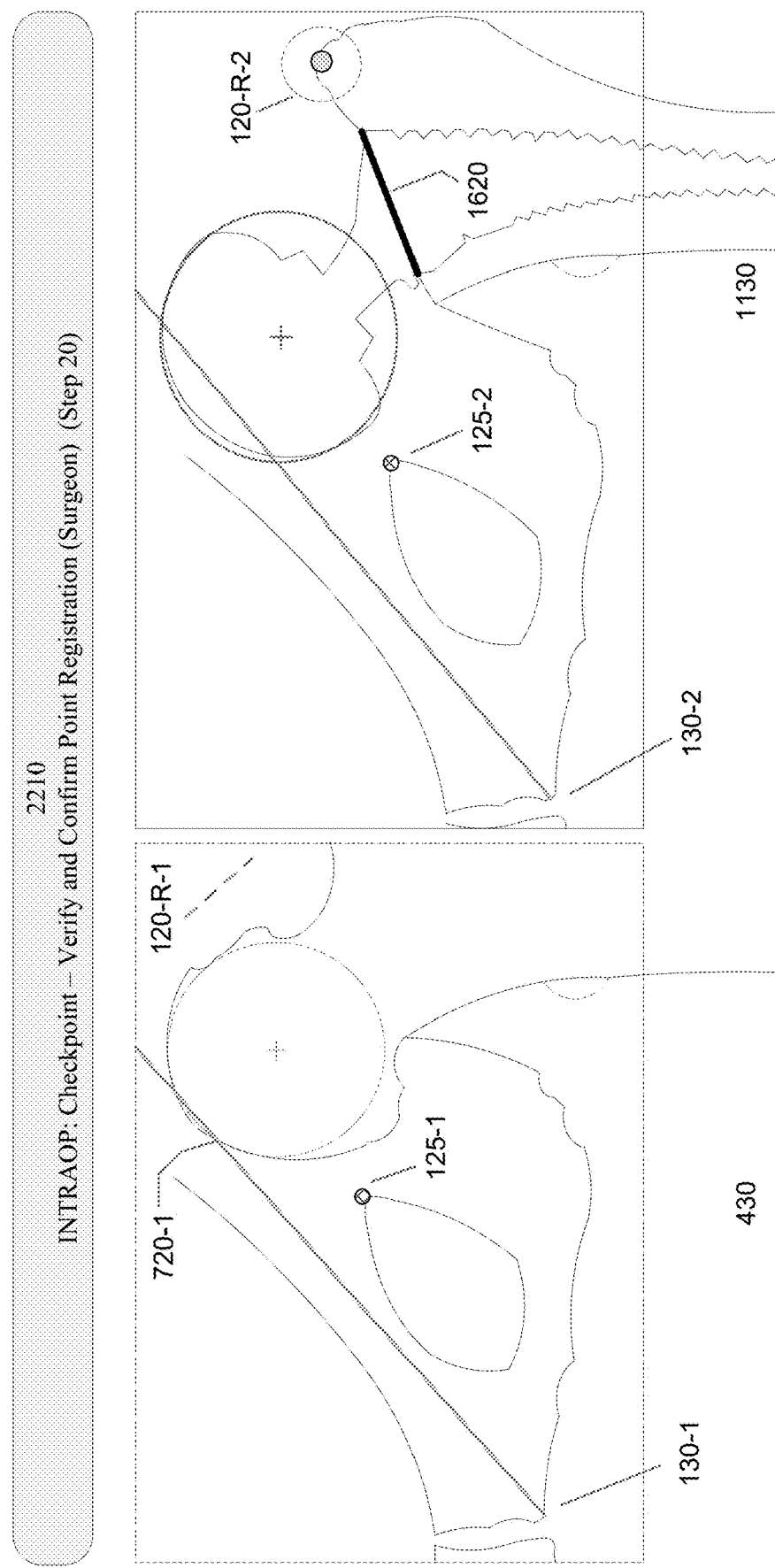
FIG. 22 shows a GUI, which may be used to confirm detected features and reference lines in preoperative and intraoperative images prior to determination of various biomechanical parameters.

FIG. 22 shows GUI 2200, which may be used to confirm detected features and reference lines in preoperative image 430 (on the left) and intraoperative image 1130 (on the right) prior to determination of various biomechanical parameters.

GUI 2200 displays the current operation shown as "INTRAOP: Checkpoint—Verify and Confirm Point Registration (Surgeon)," instructing the operator to confirm detected features and reference lines in preoperative image 430 and intraoperative image 1130.

In some embodiments, upon confirmation, the annotated preoperative image 430 and intraoperative image 1130 may be saved. FIG. 22 also shows a legend in window 2230 indicating the representations used for the various features and reference lines being confirmed. As shown in FIG. 22, the operator is being instructed to confirm locations of TD-Rs 125-1 and 125-2, pelvic reference lines 720-1 and 720-2, GT-R-1 120-R-1 (not shown in FIG. 22) and GT-R-2 120-R-2, and hip prosthesis shoulder 1620.

Figure 23:
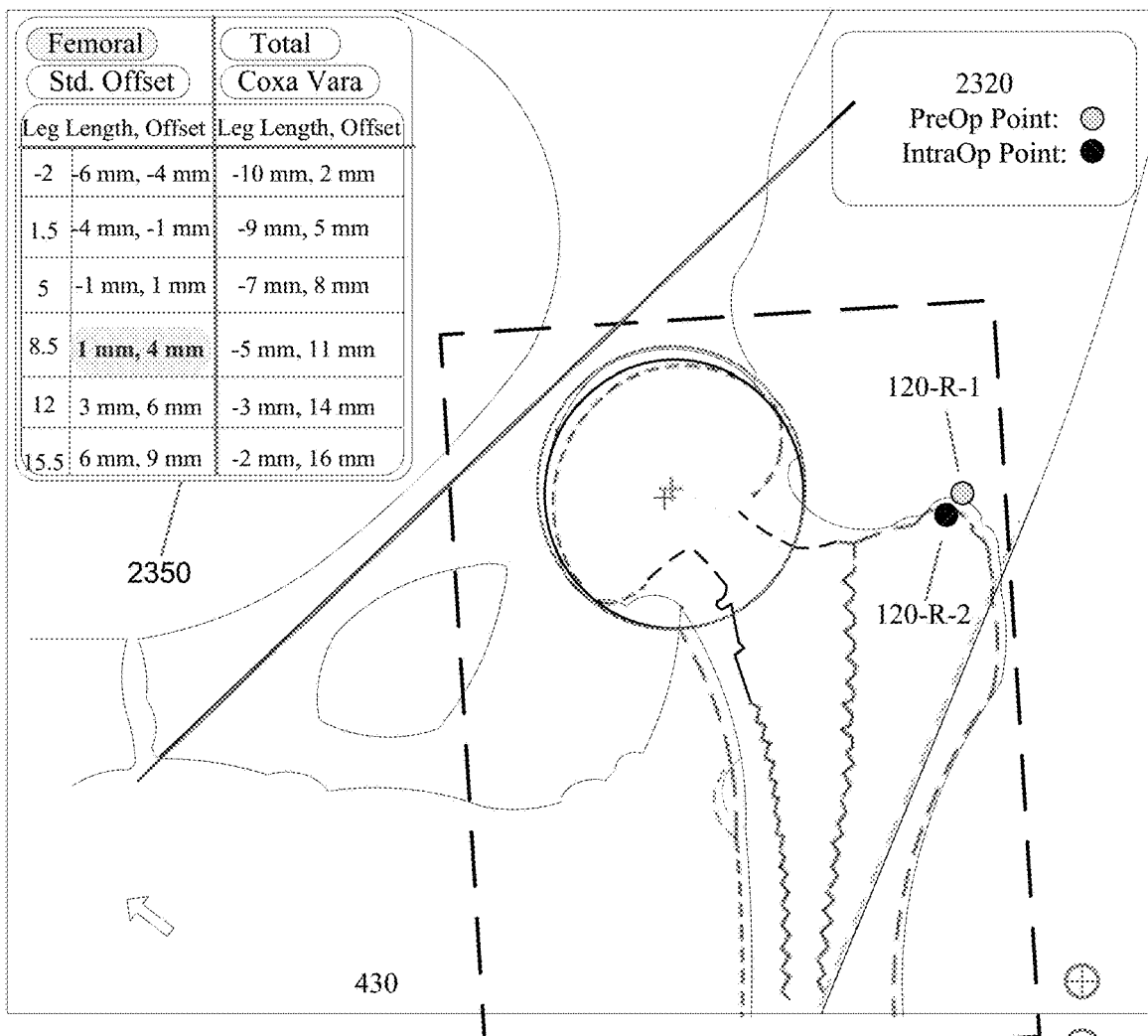
FIG. 23 shows a GUI, which includes an intraoperative analysis chart that outlines changes in leg length and offset corresponding to various femoral stem selections.

FIG. 23 shows GUI 2300, which includes an intraoperative analysis chart 2320 that outlines changes in leg length and offset corresponding to various femoral stem selections. GUI 2200 displays the current operation shown as "INTRAOP: Trial Analysis," in window 2310 and also shows that "Trial" has been selected. Window 2320 shows a legend indicating representation of preoperative and intraoperative points in the overlaid images.

Chart 2350 provides changes in leg length and offset, if the surgeon were to replace or otherwise modify the femoral stem prosthetic intraoperatively. As an alternative to a chart 2350, the system may generate a recommended femoral stem change based on a input of the surgeon's desired offset and leg length parameters. If the surgeon wants to lengthen the leg by 7 millimeters and not change offset, for example, the system will calculate leg length and offset for all femoral stem options contained in the system, and would present the femoral stem selections that would come closest to accomplishing this. Chart 2350 shows femoral stem selection 8.5 with the leg length differential indicated as 1 mm with an offset of 4 mm.

In some embodiments, the system may generate chart 2350 (or recommendations) based on a vector between at least one identifiable point on the femoral anatomy, such as the greater trochanter point (GT-R-1 120-R-1 and GT-R-2 120-R-2) identified previously, and an assumed stationary point on the femoral template, such as the center of rotation of femoral stem shoulder 1620. When the surgeon implants a different femoral stem, to generate the chart 2350, the position of the identified point on the femoral template cannot change (or changes minimally). Thus, the center of rotation of stem shoulder 1620 may be an ideal point for such an approximation.

Window 2325 shows other information indicating from Overlay Analysis that the leg length differential was determined as 1 mm, and the selected components were acetabular cup 54 mm of neutral type, with a stem size 11, standard offset, and a head length of 8.5. GUI 2330 facilitates user adjustment of overlay transparency. The user may analyze another image using GUI 2325.

Figure 24A:
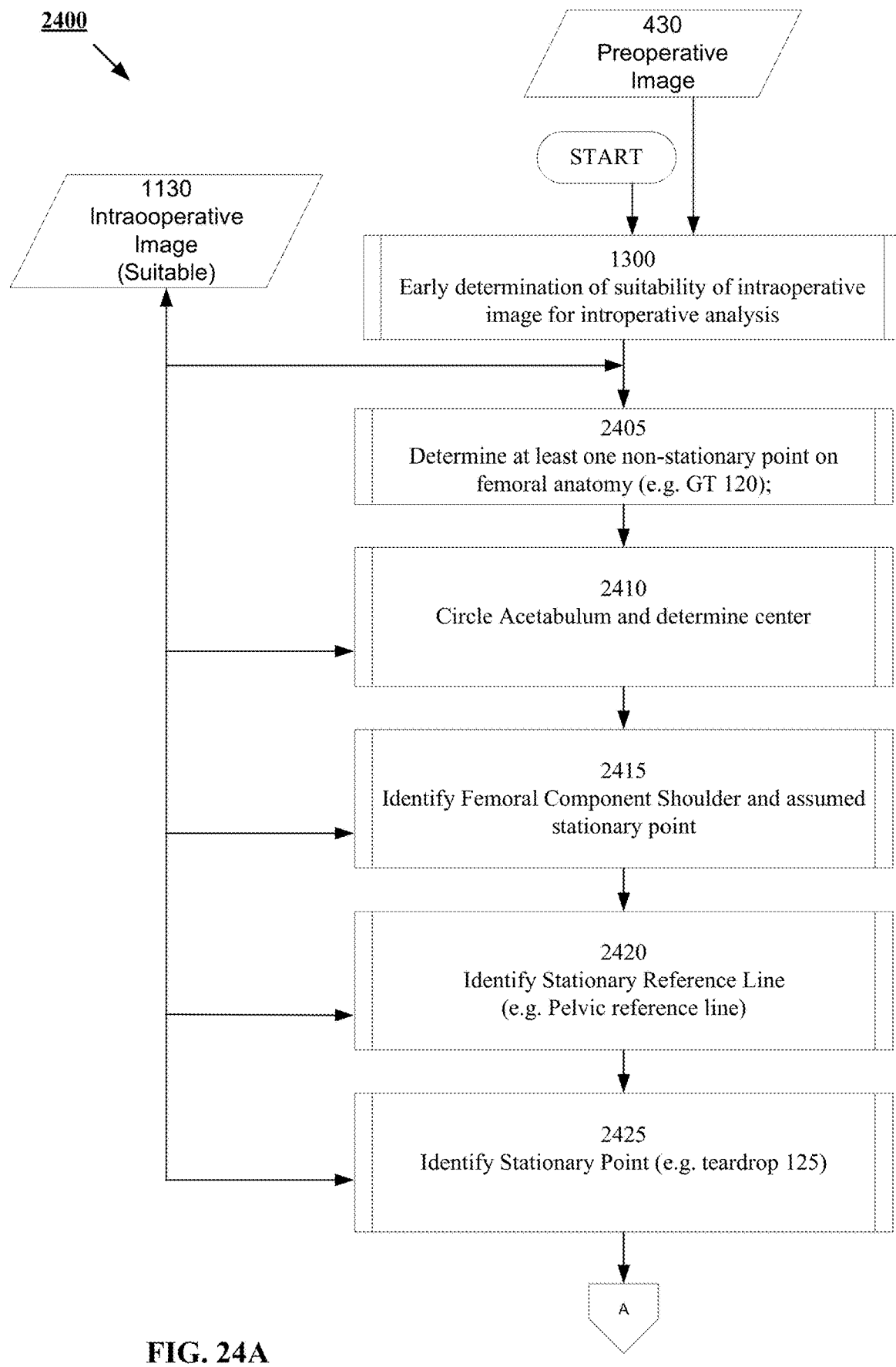
FIGS. 24A and 24B show a flowchart illustrating a method for performing intraoperative analysis on a suitable intraoperative image.
Figure 24B:
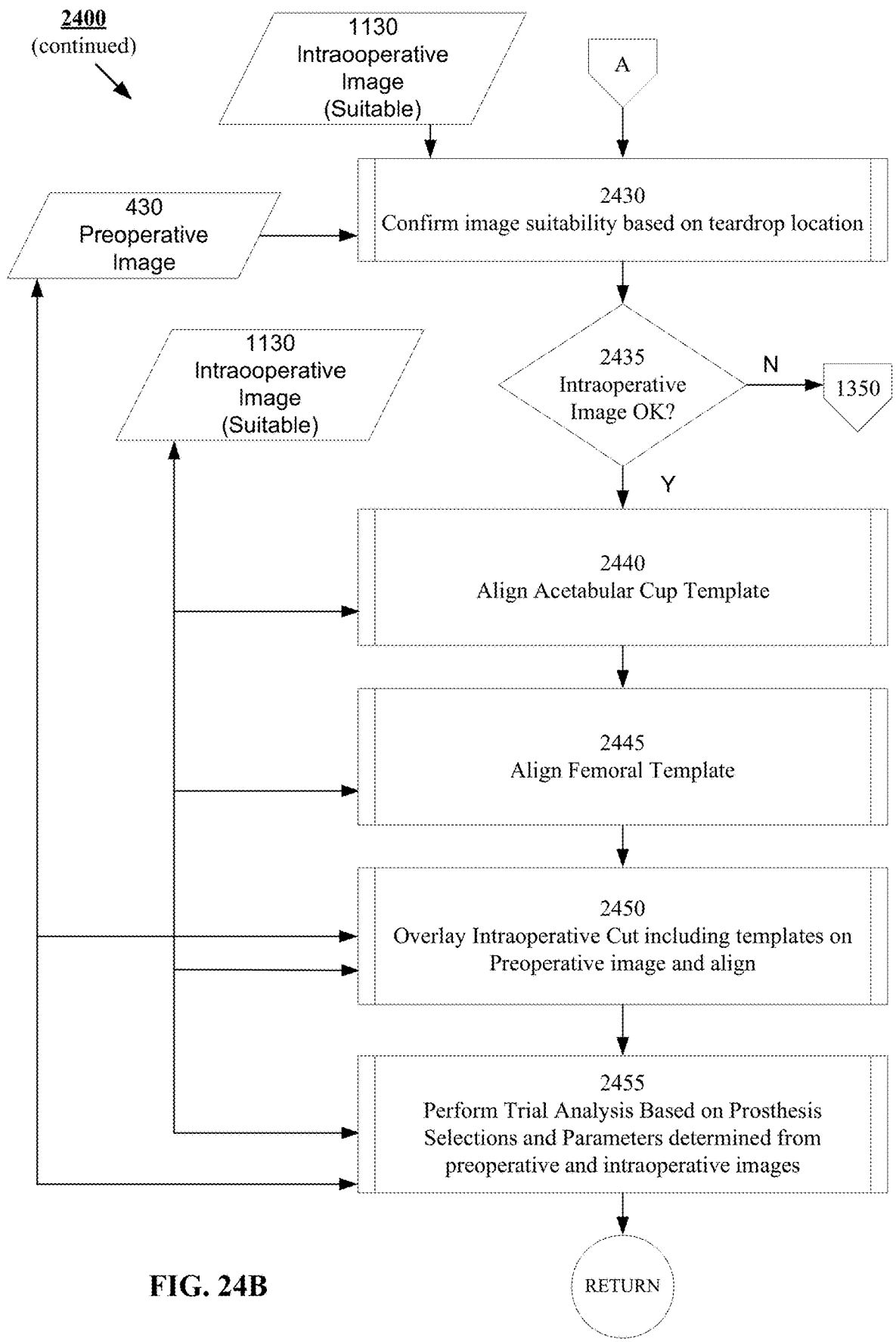

FIGS. 24A and 24B show a flowchart illustrating a method 2400 for performing intraoperative analysis on a suitable intraoperative image. In some embodiments, method 2400 may be performed on a processor, computer, or computing device, which may be coupled to an imaging device such as a fluoroscopic imaging device, and to a display.

In routine 1300, the suitability of intraoperative image 1130 for further intraoperative analysis may be determined (e.g. as outlined in relation to FIG. 13).

In response to a determination that intraoperative image 1130 is suitable, in block 2405, at least one feature point (e.g. on GT-R-2 120-R-2) on a non-stationary anatomic region (such as on femur F 150) in intraoperative image 1130 may be determined. The non-stationary point (e.g. on GT-R-2 120-R-2) may be used in subsequent step to model how changes to an implant in at least one dimension, may affect offset and leg length, which can help surgical decision making before actual change are made.

In block 2410, circle 1520 may be drawn around the acetabulum in intraoperative image 1130. The circle may facilitate a determination (e.g. based on known anatomical data) of size and other parameters related to an actual prosthetic component (e.g. an acetabular component) as well as a center of rotation for the component. These parameters may be used to scale intraoperative image 1130 and preoperative image 430 in a consistent manner.

In block 2415, femoral component shoulder 1620 may be identified. In addition, in some embodiments, at least one assumed stationary point on femoral component shoulder 1620 may be identified—such as the center of rotation of femoral stem shoulder 1620. The assumed stationary point on the femoral component shoulder may remain substantially stationary even a different femoral stem is implanted thereby facilitating modeling.

In block 2420, a stationary reference line such as pelvic reference line 720-2 on intraoperative image 1130 may be determined. Pelvic reference line 720-2 may be used (in conjunction with pelvic reference line 720-1 in preoperative image 430) and other features to scale and align intraoperative image 1130 with preoperative image 430 and/or to facilitate the overlaying and alignment of intraoperative image 1130 on preoperative image 430.

In block 2425, a stationary point such as teardrop TD-R-2 125-R-2 on intraoperative image 1130 may be identified.

Referring to FIG. 24B (which is a continuation of method 2400), in some embodiments, in block 2430, additional confirmation of the suitability of intraoperative image 1130 for further intraoperative analysis may be determined based on the location of teardrop TD-R-2 125-R-2 in intraoperative image 1130. For example, a preoperative teardrop angle may be determined based on the angle between a reference line 1820-1 (FIG. 18B, from PS 130-1 to TD 125-R-1) and another reference line such as pelvic reference line 720-1 in preoperative image 430. A corresponding intraoperative teardrop angle may be determined in intraoperative image 1130 based on the angle between reference line 1820-2 (FIG. 18B, from PS 130-2 to TD 125-R-2) and another reference line such as pelvic reference line 720-2. When the absolute value of the difference between the preoperative TD angle and the corresponding intraoperative TD angle exceeds a threshold, the user may be instructed that current intraoperative image is not suitable for further intraoperative analysis. Because of image suitability analysis performed in block 1300 performed at the time of capture of intraoperative image 1130, the likelihood of an intraoperative image unsuitability determination in block 2430 is significantly decreased.

In block 2435, in the unlikely event of an intraoperative image unsuitability determination ("N" in block 2435), block 1350 (FIG. 13) may be invoked, where the user may instructed to "Retake the X-Ray" and the warning may further indicate that C-arm position (e.g. relative to an anatomical feature of interest such as TD 125) at the time of capture of intraoperative image 1130 does not correspond to the C-arm position at the time of capture of the preoperative image. In some embodiments, the guidance may be based on whether the preoperative TD angle exceeds the corresponding intraoperative TD angle or vice versa (e.g. whether the corresponding intraoperative TD angle exceeds the preoperative angle). Accordingly, the user may be instructed to "Tilt C-Arm Cephalod Toward Feet" or to "Tilt C-Arm Cephalod Toward Head" based on the angular difference and the magnitudes of the preoperative TD angle and the corresponding intraoperative TD angle. Thus, when the intraoperative image is determined not to be suitable, the operator is provided an indication of: (a) the error, (b) an indication of whether the intraoperative TD angle is too low or too high, and (c) C-arm repositioning instructions. As outlined herein, the C-arm repositioning instructions (when the image is to be retaken) may be based on any appropriate salient anatomical patient features visible to the operator and providing clear guidance on the positioning/repositioning of the imaging apparatus.

In block 2435, in the (more likely) event that the intraoperative image is suitable, ("Y" in block 2435), then block 2440 may be invoked.

In block 2440, digital acetabular component template 230-T (which may form part of digital template image of hip prosthesis 200 and based on user selected size, type and other parameters) may be aligned with acetabular cup 230 used to obtain the digital acetabular component template 230-T. Digital acetabular component template 230-T may be superimposed over acetabular component 230 in intraoperative image 1130 and rotated, repositioned, and/or aligned to match with underlying acetabular component 230.

When intraoperative image is suitable, TD-R-2 125-R-2 may also be used as the origin of a vector that terminates at the center of rotation of acetabular component 230 in the intraoperative image and corresponds to a similar vector in the preoperative image 430. In some embodiments, subsequent steps may use the above vectors to position an acetabular component template or a representative digital annotation, such as a digital line or digital circle, in preoperative image 430 based on the above vector.

In block 2445, femoral template 240-T (e.g. based on size, type and other user selected parameters) may be aligned with the femur F 150-R-2 in the intraoperative image 1130. digital femoral template 240-T may be superimposed over femur F 155 in intraoperative image 1130 and rotated, repositioned, and/or aligned to match with underlying femur F 150. The femoral stem (240) and acetabular component (230) templates generated on the intraoperative image 1130 are connected at the center of rotation (e.g. as described in relation to FIG. 2) and may be used to model the actual positioning of the (to be implanted) prosthetic femoral stem and acetabular components. In some embodiments, in block 2445, the center of rotation of the aligned femoral template 240-T and at least one additional feature point on the femoral anatomy identified in intraoperative image 1130 and preoperative image 430 (e.g. a point GT 120 identified in block 2405) may be used to model estimated changes to offset and leg length—if a surgeon were to change femoral stem implant selection using available replacement prosthetics.

In block 2450, intraoperative image cutout 1130-C may be overlaid on preoperative image 430 to align femurs in the two images. Once intraoperative image 1130-C has been overlaid and femoral alignment completed, the system may generate femoral template 220-T so that its position and orientation in intraoperative cutout 1130-C is consistent with how femoral template 220-T was positioned in the intraoperative image (e.g. as in FIG. 20). In some embodiments, the system may remove intraoperative cutout 1130-C, while retaining the (generated) femoral template 220 overlaid on the preoperative image 430. In some embodiments, block 2450 may include a confirmation step to confirm that detected features and reference lines in preoperative image 430 and intraoperative image 1130 are correct.

In block 2455, trial analysis and/or other operations may be performed based on prosthesis selections and surgeon provided parameters to determine various anatomical and biomechanical parameters. For example, one or more of leg length differential, offset, or acetabular anteversion, or acetabular inclination, or parameters indicative of centers of rotation, or acetabular retroversion, or some combination of the above may be determined in block 2455. In some embodiments, in block 2455, femoral stem selections may be suggested based on input of the surgeon's desired offset and leg length parameters.

Figure 25:
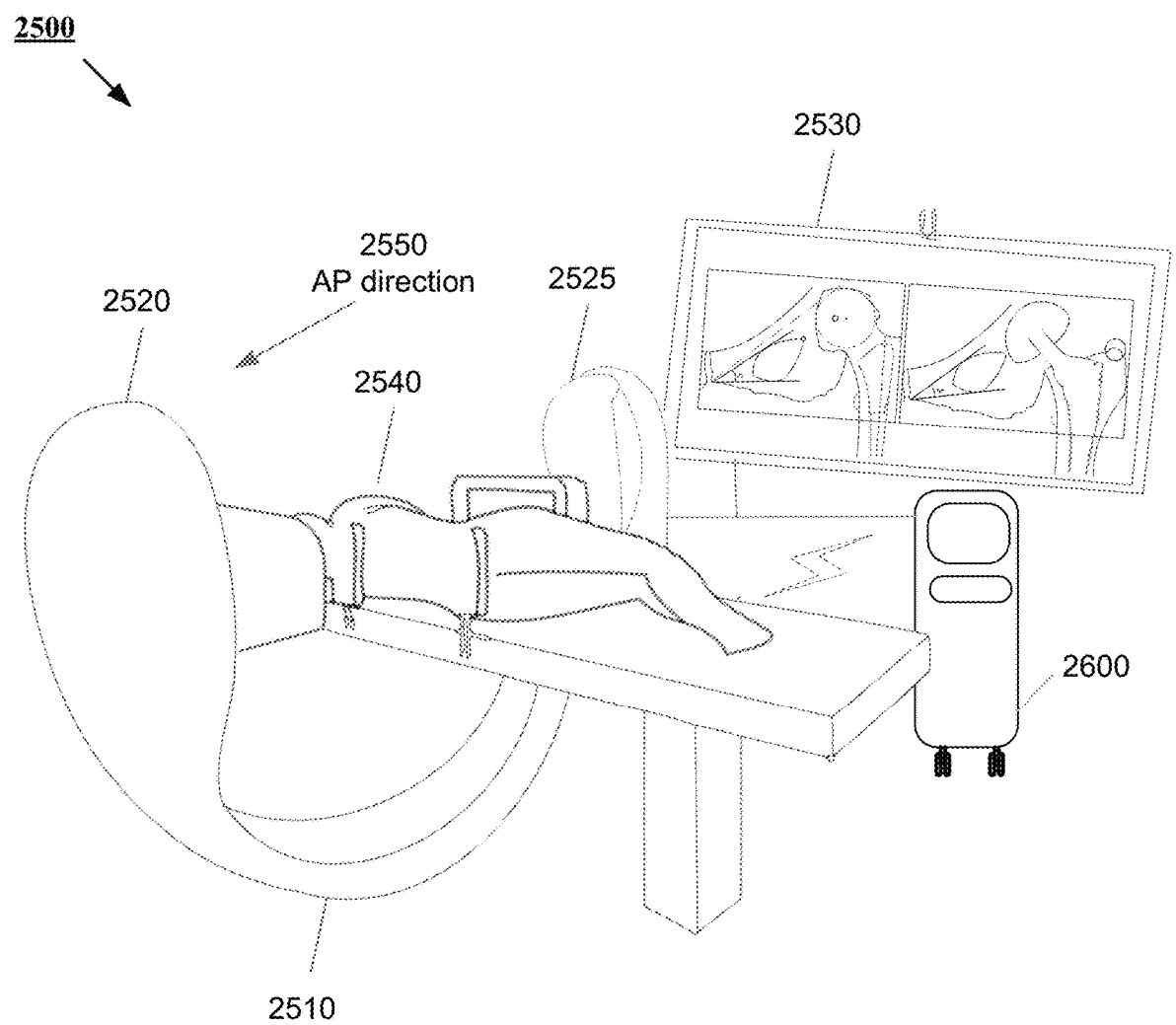
FIG. 25 depicts an example system for intraoperative analysis in accordance with certain disclosed embodiments.

FIG. 25 depicts an example system 2500 for intraoperative analysis in accordance with certain disclosed embodiments. In some embodiments, system 2500 may include C-arm fluoroscopy imaging apparatus (hereinafter "C-arm") 2510, which may be capable of motion with several degrees of freedom. Although. FIG. 25 shows C-arm 2510 as an example fluoroscopy imaging apparatus, the techniques disclosed herein may be applied to any intraoperative fluoroscopic apparatus that is capable of pose changes relative to patient 140 undergoing surgery and/or relative to an area of interest being imaged.

In some embodiments, C-arm 2510 may be coupled to X-ray source 2525, which may generate X-rays with images being captured at detector 2520. The motion of C-arm 2510 may be controlled by a control system, which may include processors and actuators, which, in some instances (e.g. when C-arm 2510 is robotic) may be responsive to commands from computer 2600. Images captured by C-arm 2510 may be transmitted over a communication network (which may be wired or wireless) to computing subsystem 2600, which may store, process, and display the raw and/or processed images on display 2530.

In some embodiments, an operator may control the movement of C-arm 2525. For example, guidance on display 2530, may instruct an operator to tilt the C-arm in a specified direction to capture an intraoperative image, indicate suitability of capture images, and/or perform various other operations (e.g. as outlined in relation to FIGS. 13 and 24). The guidance may be provided relative to salient visible anatomical features on patient 2540 (e.g. head, feet, etc.). In FIG. 25, arrow 2550 indicates the anterior-posterior (AP) direction relative to patient 2540. In FIG. 25, patient 2540 is shown as human. However, disclosed techniques may also be used with other animal subjects.

In some embodiments, computing subsystem 2600 may provide angular differences and/or angular magnitudes to C-arm 2510. For example, computer 2600 may provide one or more of: (a) a magnitude of the preoperative obturator angle, (b) a magnitude of the intraoperative obturator angles, (b) a difference between preoperative obturator angle and intraoperative obturator angle, (c) a magnitude of the preoperative teardrop angle, (e) a magnitude of the intraoperative teardrop angles and/or (d) a difference between preoperative teardrop angle and intraoperative teardrop angle. In some embodiments, (e.g. when C-arm is robotic), C-arm 2510 may use the received angular information to make appropriate adjustments to the C-arm relative to its position at the time of capture of the last intraoperative image. In other embodiments, such as when an operator exercises control over C-arm motion, the operator may be instructed and guided via messages, and or via visual indications on display 2530 on operations to be performed on C-arm 2510.

In some embodiments, display 2530 may include touchscreen functionality to facilitate user input to computing subsystem 2600. Display 2530 may thus serve as both an input and output device. Thus, display 2530 may include functionality for user manipulation of displayed images, entering of user annotations, facilitating user menu selections, etc. In some embodiments, display interface may generate graphics, and/or other visualization, which may augment or overlay the stored and captured images. In some embodiments, display 2530 may further be coupled to another input device (such as a keyboard, mouse, joystick, game controller, tablet, etc.), which may be remotely situated from display 2530. Input from the remote input device may be processed by computing subsystem 2600 and reflected on display 2530.

Figure 26:
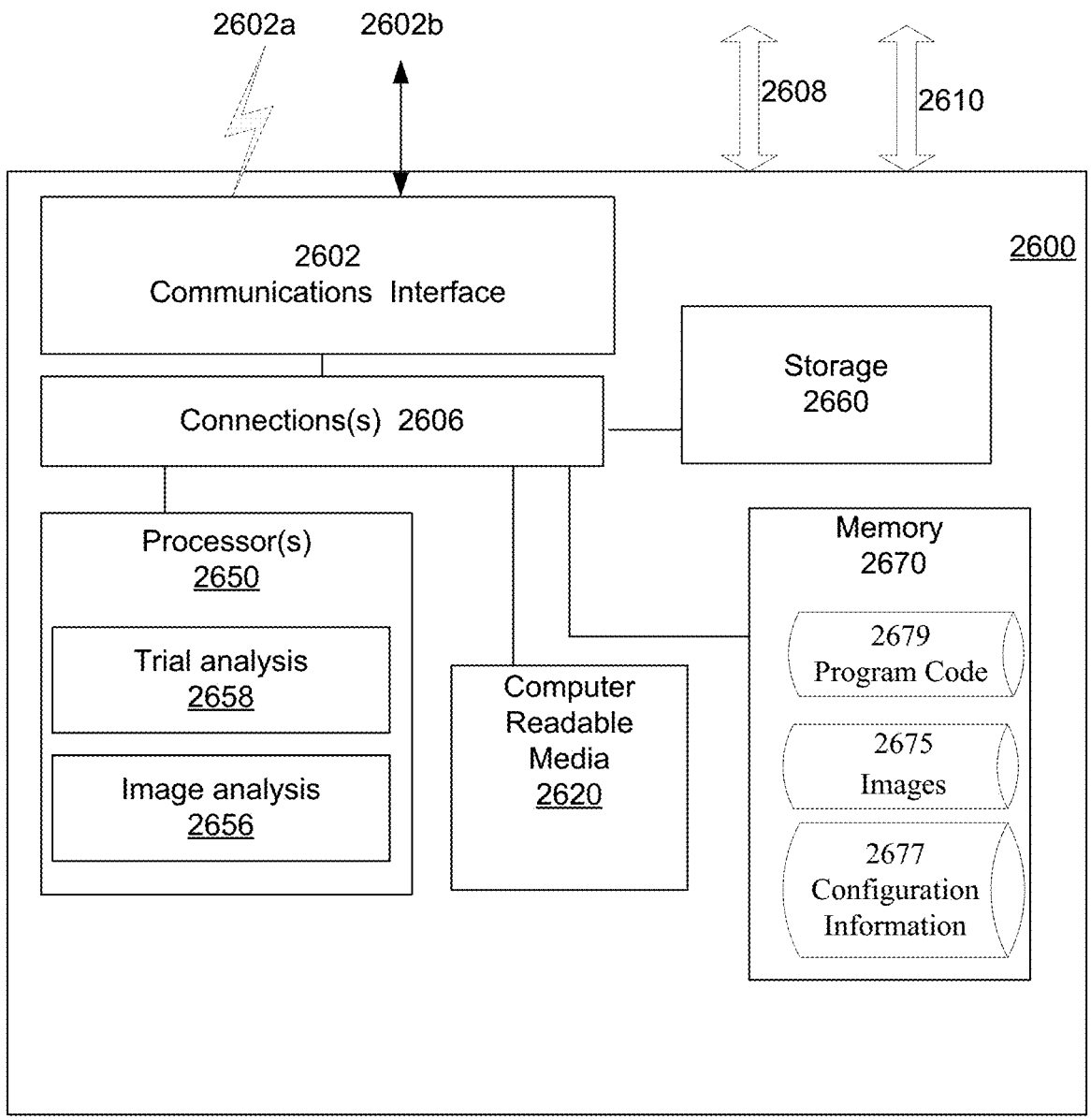
FIG. 26 depicts an example computing subsystem, to facilitate preoperative and intraoperative analysis in accordance with certain disclosed embodiments.

FIG. 26 depicts an example computing subsystem 2600, to facilitate preoperative and intraoperative analysis in accordance with certain disclosed embodiments. Computing subsystem 2600 may form a part of an intraoperative medical system (e.g. as shown in FIG. 25) and may be coupled to one or more imaging devices including C-arm devices. In some embodiments, computing subsystem 2600 may receive images from the imaging devices (e.g. C-arm 2510) and/or request or trigger the capture of new preoperative and/or intraoperative images (e.g. when an image is determined to unsuitable). Computing subsystem 2600 may be capable of performing the methods disclosed herein including the methods 1300 and/or 2400.

As shown in FIG. 26, computing subsystem 2600 may include processor(s) 2650, memory 2670, and communications interface 2602, which may be connected using connections 2606. Connections 2606 may take the form of buses, lines, fibers, electronic interfaces, links, etc., which may operationally couple the above components.

Communications interface 2602 may be capable of wired (e.g. using wired communications interface 2602b) and/or wireless (e.g. using wireless communication interface 2602a) communications with another device or component (e.g. C-arm 2510, a remote server, a private cloud, etc.). In some embodiments, captured images (e.g. preoperative images 430 and intraoperative images 1130), imaging system (e.g. C-arm 2510) state (which may include a current or previous pose of X-ray source 2525), etc., may be received over communications interface 2602 and stored in memory 2670 and/or displayed using display 2530. Wired communication may occur over wired networks. Wireless communication may include communication over Wireless Local Area Networks (WLAN), which may be based on the IEEE 802.11 standards, and/or over Wireless Wide Area Networks (WWAN), which may be based on cellular communication standards such as a Fifth Generation (5G) network, or Long Term Evolution (LTE).

In some embodiments, computing subsystem 2600 may include a user interface (e.g. through touchscreen on display 2530), which may facilitate user input (e.g. to store, select, manipulate, annotate, compare, analyze, and/or overlay images, provide commands, invoke programs, and/or to exercise other functionality) provided by computing subsystem 2600. In some embodiments, optional control interface 2608 may be used communicate with processor(s) 2650 and C-arm 2510, and may be used by processor(s) 2650 to exchange command and control information with C-arm 2510.

Computing subsystem 2600 may also include display interface 2610, which may interact with display 2530 to provide visual feedback (e.g. configuration information, display preoperative images 430, display intraoperative images 1130, display procedure related information, system state information, etc.). In some embodiments, display 2530 may include touchscreen functionality to facilitate user input. Thus, display 2530 may include functionality for user manipulation of displayed images, entering of user annotations, facilitating user menu selections, etc. In some embodiments, display interface may relay computer generated graphics, and/or other visualizations, which may augment or overlay the stored and captured images. Display interface 2610 may communicate with processor(s) 2650 and may be controlled by processor(s) 2650. In some embodiments, computing subsystem, 2600 may also be coupled to another input device to facilitate user input, which may be reflected on display 2530.

In some embodiments, memory 2670 may comprise main or primary memory (e.g. RAM) and storage 2660 (e.g. hard disks, solid state memory, optical media, etc.). Program code 2679 may be stored in memory 2670, and read and executed by processor(s) 2650 to perform the techniques disclosed herein. Storage 2660 may include ROM, EPROM, NVRAM, flash memory, solid state memory, other secondary storage, and other computer readable media (e.g. fixed and/or removable drives, optical disks, etc.). Computer-readable media 2620 may be encoded with databases, data structures, data, etc. and/or with computer programs. By way of example, and not limitation, such computer-readable media may also include CD-ROM, memory cards, portable drives, or other optical disk storage, magnetic disk storage, solid state drives, other storage devices, or any other medium that can be used to store desired program code in the form of instructions and/or data structures and that can be accessed by a computer.

Memory 2670 may store images (preoperative and intraoperative, including with user annotations, and/or other augmentations), patient data, anatomical measurements, databases pertaining to prosthetics, etc. Memory 2670 may include configuration information 2677, which may provide information pertaining to program settings, user profile information, user preferences, etc.

The methodologies described herein may be implemented in hardware, firmware, software, or any combination thereof. For a hardware implementation, the processor(s) 2650 may be implemented within one or more application specific integrated circuits (ASICs), digital signal processors (DSPs), image processors, digital signal processing devices (DSPDs), programmable logic devices (PLDs), field programmable gate arrays (FPGAs), processors, controllers, micro-controllers, microprocessors, electronic devices, other electronic units designed to perform the functions described herein, or any combination thereof. In some embodiments, processor(s) 2650 may include capabilities to perform one or more of: image analysis to determine and label features, compare images, use anatomical and/or other provided information in conjunction with image features to estimate sizes, distances, centers of rotation, and/or angles between image features, overlay images, perform real time image manipulation in response to user input to scale, rotate, and align images, and/or perform other functions outline in methods disclosed herein (e.g. such as methods 1300 and/or 2400), etc. In some embodiments, the functions above may be performed using image analysis engine 2656. In some embodiments, processor(s) 2650 may also include Trial Analysis engine 2658, which may estimate bio-mechanical parameters and/or anatomical effects from use of or changes to prosthesis or prosthetic components. In some embodiments, Trial Analysis engine 2658 may use information determined by Image Analysis engine 2656 (e.g. sizes, distances, feature locations, centers of rotations, reference lines, etc.) along with known patient anatomical information, and information pertaining to prosthetics and prosthetic components when estimating bio-mechanical parameters and/or anatomical effects.

Although the present disclosure is described in connection with specific embodiments for instructional purposes, the disclosure is not limited thereto. Various adaptations and modifications may be made to the disclosure without departing from the scope. Therefore, the spirit and scope of the appended claims should not be limited to the foregoing description.

What is claimed is:

1. A processor-implemented method to intraoperatively determine a suitability of an intraoperative image for further intraoperative surgical analysis, the method comprising:
    determining, based on at least three pelvic feature points in a pre-operative image, a first angle;
    determining, based on at least three corresponding pelvic feature points in a first intraoperative image, a corresponding second angle;
    determining the suitability of the intraoperative image for the further intraoperative surgical analysis based on a comparison of the first angle and the corresponding second angle; and
    in response to a determination that the first intraoperative image is not suitable for the intraoperative surgical analysis, providing an indication of a movement direction for a fluoroscopy camera used to obtain the first intraoperative image.

2. The method of claim 1, further comprising providing an indication that the first intraoperative image is not suitable for the further intraoperative surgical analysis.

3. The method of claim 1, wherein the first angle is a first obturator angle and the corresponding second angle is a corresponding second obturator angle.

4. The method of claim 3, wherein:
    the first obturator angle is formed at an inferior pubic symphysis (PS) in the preoperative image by intersection of a first upper reference line from the inferior PS to a first upper feature point on a upper boundary of an obturator foramen (OF) in the preoperative image and a first lower reference line from the inferior PS to a first lower feature point on a lower boundary of the OF in the preoperative image; and
    the corresponding second obturator angle is formed at the inferior PS in the intraoperative image by intersection of a corresponding second upper reference line from the inferior PS to a corresponding second upper feature point on the upper boundary of the OF in the first intraoperative image and a corresponding second lower reference line from the inferior PS to a corresponding second lower feature point on the lower boundary of the OF in the first intraoperative image.

5. The method of claim 1, wherein the first intra-operative image is indicated as suitable for further intraoperative surgical analysis when an absolute value of a difference between the first angle and the corresponding second angle does not exceed a threshold.

6. The method of claim 1, wherein the indication of the movement direction for the fluoroscopy camera is provided when an absolute value of a difference between the first angle and the corresponding second angle exceeds a threshold.

7. The method of claim 6, wherein the indication of the movement direction includes directional instructions for movement of the fluoroscopy camera relative to salient anatomical features of a surgical subject.

8. The method of claim 1, wherein the indication of the movement direction for the fluoroscopy camera is relative to pose of the fluoroscopy camera at the time of obtaining the first intraoperative image.

9. The method of claim 1, further comprising providing an indication of non-suitability and one or more of: an angular difference between the first angle and the corresponding second angle, or a measurement of the first angle and a measurement of the second angle to a fluoroscopy imaging apparatus, wherein the fluoroscopy camera is coupled to the fluoroscopy imaging apparatus.

10. The method of claim 9, further comprising receiving, in response to the indication of non-suitability, an indication of capture of a second intraoperative image.

11. The method of claim 1, wherein the method is triggered on receipt of the first intraoperative image.

12. The method of claim 1, wherein the method is performed intraoperatively during a hip arthroplasty procedure and, in response to a determination of suitability of the first intraoperative image, further intraoperative surgical analysis comprises determination of at least one of: leg length offset, or acetabular anteversion, or acetabular inclination, or parameters indicative of centers of rotation, or acetabular retroversion, or a combination thereof.

13. An apparatus comprising:
a communications interface to receive a first intraoperative image captured by a fluoroscopy camera,
a memory capable of storing a preoperative image and the first intraoperative image, and
a processor coupled to the memory and the communications interface, wherein the processor is configured to:
determine, based on at least three pelvic feature points in the preoperative image, a first angle;
determine, based on at least three corresponding pelvic feature points in the first intraoperative image, a corresponding second angle;
determine the suitability of the intraoperative image for further intraoperative surgical analysis based on a comparison of the first angle and the corresponding second angle; and
in response to a determination that the first intraoperative image is not suitable for the intraoperative surgical analysis, provide an indication of a movement direction for the fluoroscopy camera used to obtain the first intraoperative image.

14. The apparatus of claim 13, wherein the first angle is a first obturator angle and the corresponding second angle is a corresponding second obturator angle.

15. The apparatus of claim 14, wherein:
the first obturator angle is formed at an inferior pubic symphysis (PS) in the preoperative image by intersection of a first upper reference line from the inferior PS to a first upper feature point on a upper boundary of an obturator foramen (OF) in the preoperative image and a first lower reference line from the inferior PS to a first lower feature point on a lower boundary of the OF in the preoperative image; and
the corresponding second obturator angle is formed at the inferior PS in the intraoperative image by intersection of a corresponding second upper reference line from the inferior PS to a corresponding second upper feature point on the upper boundary of the OF in the first intraoperative image and a corresponding second lower reference line from the inferior PS to a corresponding second lower feature point on the lower boundary of the OF in the first intraoperative image.

16. The apparatus of claim 13, wherein the first intraoperative image is indicated as suitable for further intraoperative surgical analysis when an absolute value of a difference between the first angle and the corresponding second angle does not exceed a threshold.

17. The apparatus of claim 13, wherein the indication of the movement direction for the fluoroscopy camera is provided when an absolute value of a difference between the first angle and the corresponding second angle exceeds a threshold.

18. The apparatus of claim 17, wherein the indication of the movement direction includes directional instructions for movement of the fluoroscopy camera relative to salient anatomical features of a surgical subject.

19. A non-transitory computer-readable medium comprising instructions to configure a processor to:
determine, based on at least three pelvic feature points in a preoperative image, a first angle;
determine, based on at least three corresponding pelvic feature points in a first intraoperative image, a corresponding second angle;
determine the suitability of the intraoperative image for further intraoperative surgical analysis based on a comparison of the first angle and the corresponding second angle; and
in response to a determination that the first intraoperative image is not suitable for the intraoperative surgical analysis, provide an indication of a movement direction for the fluoroscopy camera used to obtain the first intraoperative image.

20. The computer-readable medium of claim 19, wherein the first angle is a first obturator angle and the corresponding second angle is a corresponding second obturator angle.

* * * * *